(12) United States Patent
Huang et al.

(10) Patent No.: US 11,690,922 B2
(45) Date of Patent: Jul. 4, 2023

(54) LIPID COMPOUND AS WELL AS LIPID CARRIER, NUCLEIC ACID LIPID NANOPARTICLE COMPOSITION AND PHARMACEUTICAL PREPARATION CONTAINING SAME

(71) Applicant: Purecodon (Hong Kong) Biopharma Ltd., Hong Kong (CN)

(72) Inventors: Ke Huang, Suzhou (CN); Binxi Ge, Suzhou (CN); Yingwen Li, Suzhou (CN); Yuping Liu, Suzhou (CN); Yinjia Gao, Suzhou (CN); Zhenhua Sun, Suzhou (CN)

(73) Assignee: Purecodon (Hong Kong) Biopharma Ltd., Hong Kong (CN)

( * ) Notice: Subject to any disclaimer, the term of this patent is extended or adjusted under 35 U.S.C. 154(b) by 0 days.

(21) Appl. No.: 17/870,313

(22) Filed: Jul. 21, 2022

(65) Prior Publication Data

US 2023/0093138 A1    Mar. 23, 2023

(30) Foreign Application Priority Data

Jul. 21, 2021   (CN) ........................ 202110821782.5

(51) Int. Cl.

| | | |
|---|---|---|
| A61K 48/00 | (2006.01) | |
| A61K 47/10 | (2017.01) | |
| A61K 31/713 | (2006.01) | |
| A61K 9/127 | (2006.01) | |
| A61K 9/14 | (2006.01) | |
| C07C 217/08 | (2006.01) | |
| C07C 219/06 | (2006.01) | |
| C07C 229/16 | (2006.01) | |
| C07C 233/18 | (2006.01) | |
| C07C 233/36 | (2006.01) | |
| C07C 237/12 | (2006.01) | |
| C07C 323/25 | (2006.01) | |
| C07C 323/52 | (2006.01) | |
| A61K 47/18 | (2017.01) | |

(52) U.S. Cl.
CPC ............ *A61K 48/005* (2013.01); *A61K 9/127* (2013.01); *A61K 9/145* (2013.01); *A61K 31/713* (2013.01); *A61K 47/10* (2013.01); *A61K 47/18* (2013.01); *A61K 48/0033* (2013.01); *C07C 217/08* (2013.01); *C07C 219/06* (2013.01); *C07C 229/16* (2013.01); *C07C 233/18* (2013.01); *C07C 233/36* (2013.01); *C07C 237/12* (2013.01); *C07C 323/25* (2013.01); *C07C 323/52* (2013.01)

(58) Field of Classification Search
CPC ..... A61K 48/005; A61K 47/18; C07C 237/12
See application file for complete search history.

(56) References Cited

U.S. PATENT DOCUMENTS

| | | |
|---|---|---|
| 2020/0129608 A1 | 4/2020 | Ciaramella et al. |
| 2023/0426942 | 2/2023 | Zuo et al. |

FOREIGN PATENT DOCUMENTS

| | | | |
|---|---|---|---|
| CN | 108368028 | 8/2018 | |
| CN | 109640962 | 4/2019 | |
| CN | 110352071 | 10/2019 | |
| CN | 110430894 | 11/2019 | |
| CN | 110740985 | 1/2020 | |
| WO | WO 2017201333 | 11/2017 | |
| WO | WO 2020/023655 | 1/2020 | |
| WO | WO 2020/257730 | 12/2020 | |
| WO | WO-2021239488 A1 * | 12/2021 | ........... C09D 11/101 |

OTHER PUBLICATIONS

Zhou, K. et al. "Modular degradable dendrimers enable small RNAs to extend survival in an aggressive liver cancer model" (PNAS 2016, 113 (3), pp. 520-525). (Year: 2016).*
Zhou et al. (PNAS 2016, 113 (3)). Supporting information, pp. 1-27 (Year: 2016).*

* cited by examiner

*Primary Examiner* — Andrew S Rosenthal
(74) *Attorney, Agent, or Firm* — Fish & Richardson P.C.

(57) ABSTRACT

The present invention belongs to the technical field of gene therapy, and particularly relates to a series of lipid compounds as well as a lipid carrier, nucleic acid lipid nanoparticle composition and pharmaceutical preparation containing the same. A compound having a structure of a formula (I) provided by the present invention can be used for preparing a lipid carrier together with other lipid compounds, and exhibits pH response, and the entrapment efficiency to a nucleic acid drug is high, which greatly improves in-vivo delivery efficiency of the nucleic acid drug; and furthermore, a lipid compound with a specific structure can be chosen as a lipid carrier based on an organ in which the nucleic acid drug needs to be enriched, having a good market application prospect.

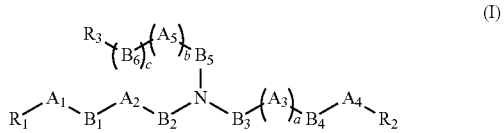

(I)

18 Claims, 4 Drawing Sheets

LIPID COMPOUND AS WELL AS LIPID CARRIER, NUCLEIC ACID LIPID NANOPARTICLE COMPOSITION AND PHARMACEUTICAL PREPARATION CONTAINING SAME

CROSS-REFERENCE TO RELATED APPLICATIONS

This application claims the benefit of Chinese Patent Application No. 202110821782.5 filed on Jul. 21, 2021, which is incorporated herein by reference for all purposes as if fully set forth herein.

TECHNICAL FIELD

The present invention belongs to the technical field of gene therapy, and particularly relates to a lipid compound as well as a lipid carrier, nucleic acid lipid nanoparticle composition and pharmaceutical preparation containing the same.

BACKGROUND

A gene therapy technology is a research hotspot in the field of modern biomedicine, use of nucleic acid drugs can prevent cancer, and bacterial and viral infections, and treat diseases having genetic cause, etc. Because the nucleic acid drugs have characteristics such as being easily degradable, and difficult to enter cells, they need to be encapsulated by means of a carrier for delivery to target cells, therefore, developing a safe and efficient delivery carrier becomes a premise of gene therapy in clinical application.

Currently, lipid nanoparticles (LNPs) are a research hotspot in the field of non-viral gene vector. In 2018, FDA approved delivery of patisiran (onpattro) by LNPs for treatment of hereditary transthyretin amyloidosis, since then the research of delivering nucleic acid drugs by using the LNP technology shows a burst of growth; especially at the end of 2020, FDA respectively approved novel coronavirus vaccines against COVID-19 from Moderna and BioNtech & Pfizer, the two vaccines both deliver mRNA drugs by the LNP technology, thereby achieving prevention against COVID-19 virus.

LNPs generally consist of four lipid compounds, i.e. cationic lipid, neutral lipid, sterol and amphiphilic lipid, wherein, selection of the cationic lipid has the greatest influence on LNPs, such as influence on entrapment efficiency of the nucleic acid drugs, in-vivo delivery efficiency of the nucleic acid drugs and cytotoxicity, etc.

In view of this, developing a novel compound which can be used as cationic lipid will be of a great significance.

SUMMARY

The Problem to be Solved by the Invention

The present invention aims to provide a series of compounds, the compounds can be used for preparing a lipid carrier together with other lipid compounds, and improves in-vivo delivery efficiency of a nucleic acid drug, and a lipid compound with a specific structure can be chosen as a lipid carrier based on an organ in which the nucleic acid drug needs to be enriched.

The present invention also provides a lipid carrier including the above-mentioned compounds.

The present invention also provides a nucleic acid lipid nanoparticle composition including the above-mentioned compounds or the above-mentioned lipid carrier.

The present invention also provides a pharmaceutical preparation including the above-mentioned compounds, or the above-mentioned lipid carrier, or the above-mentioned nucleic acid lipid nanoparticle composition.

Solution for Solving the Problem

<A First Aspect>

The present invention provides a compound of a formula (I) or a pharmaceutically acceptable salt, stereoisomer, tautomer, solvate, chelate, non-covalent complex or prodrug thereof,

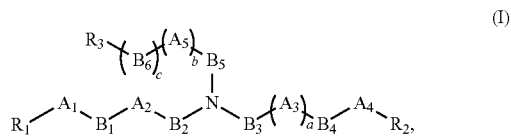

(I)

wherein:

$A_1, A_2, A_3, A_4$ and $A_5$ are each independently one or more of —O(C=O)—, —(C=O)O—, —C(=O)—, —O—, —S(O)—, —S—S—, —C(=O)S—, —SC(=O)—, —NR$^a$C(=O)—, —C(=O)NR$^a$—, —NR$^a$OC(=O)—, —OC(=O)NR$^a$— or —NR$^a$OC(=O)NR$^a$—;

$B_1, B_2, B_3$ and $B_4$ are each independently $C_{1-12}$ alkylene or $C_{2-12}$ alkenylene;

$B_5$ and $B_6$ are each independently $C_{1-24}$ alkylene, $C_{2-24}$ alkenylene, $C_{3-24}$ cycloalkylene or $C_{3-24}$ cylcoalkenylene;

$R_1$ and $R_2$ are each independently $C_{1-24}$ alkyl or $C_{2-24}$ alkenyl;

$R_3$ is hydrogen, CN, hydroxyl, hydroxyl-substituted alkyl or 5- to 7-membered heterocyclyl; wherein, the 5- to 7-membered heterocyclyl is optionally substituted by $C_{1-4}$ alkyl, and contains 1 to 4 ring-forming heteroatoms, and the heteroatoms are each independently N, O or S;

$R^a$ is hydrogen or $C_{1-24}$ hydrocarbyl; and a, b and c are each independently 0 or 1.

According to the compound of the formula (I), preferably, $R^a$ is hydrogen or $C_{1-24}$ alkyl, $A_1, A_2, A_3, A_4, A_5, B_1, B_2, B_3, B_4, B_5, B_6, R_1, R_2, R_3$, a, b and c are as defined in the formula (I).

Preferably, the compound has a structure shown in a formula (I-1):

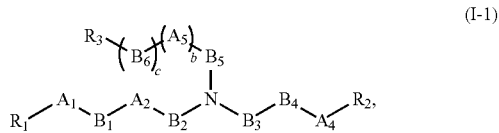

(I-1)

wherein, $A_1, A_2, A_4, A_5, B_1, B_2, B_3, B_4, B_5, B_6, R_1, R_2, R_3$, b and c are as defined in the formula (I).

Preferably, $R_3$ is hydroxyl or hydroxyl-substituted alkyl, and $A_1, A_2, A_4, A_5, B_1, B_2, B_3, B_4, B_5, B_6, R_1, R_2$, b and c are as defined in the formula (I).

More preferably, $R_3$ is hydroxyl, b and c are 0, and $B_5$ is $C_{1-8}$ alkylene.

Preferably, the compound has a structure shown in a formula (I-2):

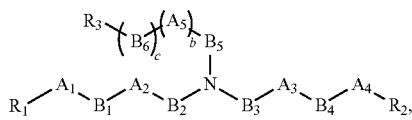
(I-2)

wherein, $A_1$, $A_2$, $A_3$, $A_4$, $A_5$, $B_1$, $B_2$, $B_3$, $B_4$, $B_5$, $B_6$, $R_1$, $R_2$, $R_3$, b and c are as defined in the formula (I).

Preferably, $R_1$ and $R_2$ are each independently $C_{4-24}$ branched alkyl or $C_{4-24}$ branched alkenyl, and $A_1$, $A_2$, $A_3$, $A_4$, $A_5$, $B_1$, $B_2$, $B_3$, $B_4$, $B_5$, $B_6$, $R_3$, b and c are as defined in the formula (I).

More preferably, $R_3$ is hydroxyl or hydroxyl-substituted alkyl, $A_1$, $A_2$, $A_3$, $A_4$, $A_5$, $B_1$, $B_2$, $B_3$, $B_4$, $B_5$, $B_6$, $R_1$, $R_2$, b and c are as defined in the formula (I-2).

According to the compound of the formula (I-2), more preferably, the compound has a structure shown in a formula (I-2-1):

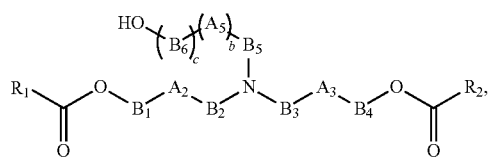
(I-2-1)

wherein, $A_2$, $A_3$, $A_5$, $B_1$, $B_2$, $B_3$, $B_4$, $B_5$, $B_6$, $R_1$, $R_2$, b and c are as defined in the formula (I-2).

According to the compound of the formula (I-2-1), preferably, $A_5$ is —O—, —O(C=O)— or —(C=O)O—, and $A_2$, $A_3$, $B_1$, $B_2$, $B_3$, $B_4$, $B_5$, $B_6$, $R_1$, $R_2$, b and c are as defined in the formula (I-2).

More preferably, the compound has a structure shown in a formula (I-2-1-1):

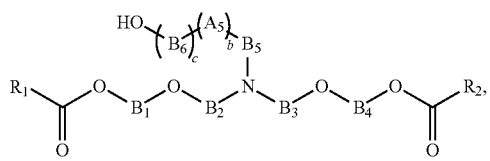
(I-2-1-1)

wherein, $A_5$, $B_1$, $B_2$, $B_3$, $B_4$, $B_5$, $B_6$, $R_1$, $R_2$, b and c are as defined in the formula (I-2-1);
or, the compound has a structure shown in a formula (I-2-1-2):

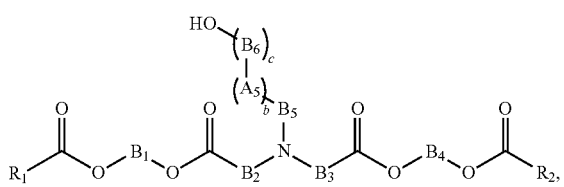
(I-2-1-2)

wherein, $A_5$, $B_1$, $B_2$, $B_3$, $B_4$, $B_5$, $B_6$, $R_1$, $R_2$, b and c are as defined in the formula (I-2-1).

More preferably, the compound has a structure shown in a formula (I-2-2):

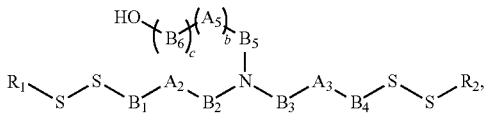
(I-2-2)

wherein, $A_2$, $A_3$, $A_5$, $B_1$, $B_2$, $B_3$, $B_4$, $B_5$, $B_6$, $R_1$, $R_2$, b and c are as defined in the formula (I-2).

According to the compound of the formula (I-2-2), preferably, $A_5$ is —O—, —O(C=O)— or —(C=O)O—, and $A_2$, $A_3$, $B_1$, $B_2$, $B_3$, $B_4$, $B_5$, $B_6$, $R_1$, $R_2$, b and c are as defined in the formula (I-2).

Particularly preferably, b is 0.

According to the compound of the formula (I-2), more preferably, $R_3$ is 5- to 7-membered heterocyclyl, wherein the 5- to 7-membered heterocyclyl is optionally substituted by $C_{1-4}$ alkyl, and contains 1 to 4 ring-forming heteroatoms, and the heteroatoms are each independently N, O or S.

More preferably, the compound has a structure shown in a formula (I-2-3):

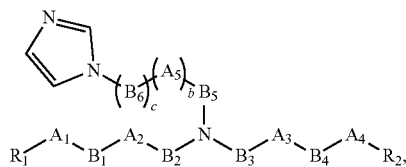
(I-2-3)

wherein, $A_1$, $A_2$, $A_3$, $A_4$, $A_5$, $B_1$, $B_2$, $B_3$, $B_4$, $B_5$, $B_6$, $R_1$, $R_2$, b and c are as defined in the formula (I-2).

According to the compound of the formula (I-2-3), preferably, $A_5$ is —O—, —O(C=O)— or —(C=O)O—, and $A_1$, $A_2$, $A_3$, $A_4$, $B_1$, $B_2$, $B_3$, $B_4$, $B_5$, $B_6$, $R_1$, $R_2$, b and c are as defined in the formula (I-2).

More preferably, the compound has a structure shown in a formula (I-2-3-1):

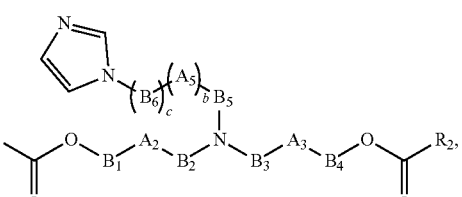
(I-2-3-1)

wherein, $A_2$, $A_3$, $A_5$, $B_1$, $B_2$, $B_3$, $B_4$, $B_5$, $B_6$, $R_1$, $R_2$, b and c are as defined in the formula (I-2-3).

Particularly preferably, b is 0.

According to the compound of the formula (I-2), more preferably, $R_3$ is hydrogen, and c is 1.

More preferably, the compound has a structure shown in a formula (I-2-4):

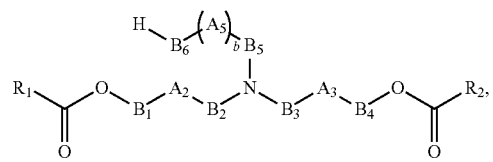

(I-2-4)

wherein, $A_2, A_3, A_5, B_1, B_2, B_3, B_4, B_5, B_6, R_1, R_2$ and b are as defined in the formula (I-2).

According to the compound of the formula (I-2-4), preferably, $A_5$ is —O(C=O)—, —(C=O)O—, —O—, —NR$^a$C(=O)— and —C(=O)NR$^a$—, wherein, R$^a$ is as defined in the formula (I-2).

<A Second Aspect>

The present invention provides the following compounds or a pharmaceutically acceptable salt, stereoisomer, tautomer, solvate, chelate, non-covalent compound or prodrug thereof:

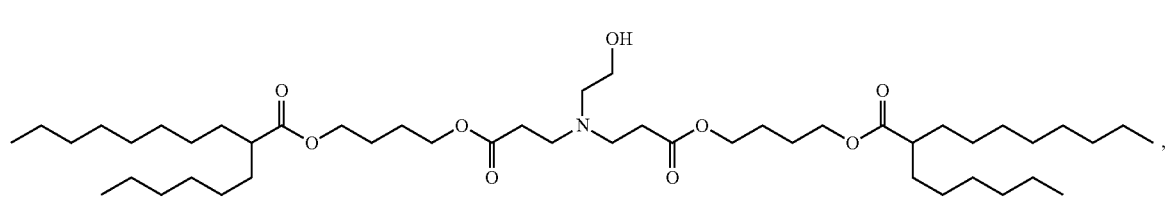

1

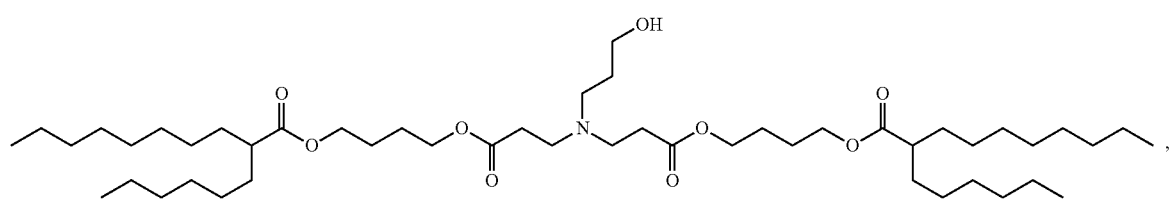

2

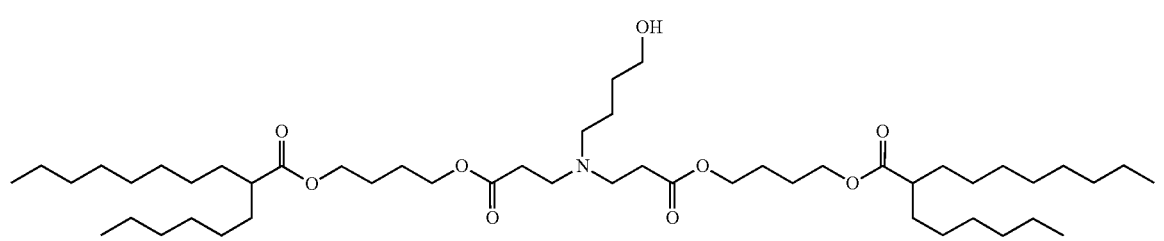

3

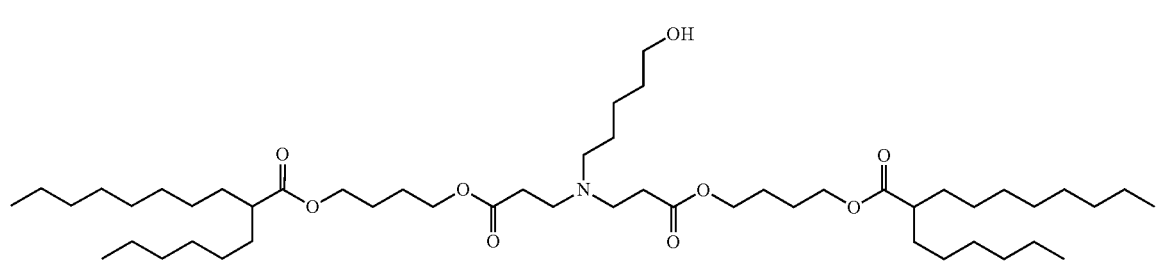

4

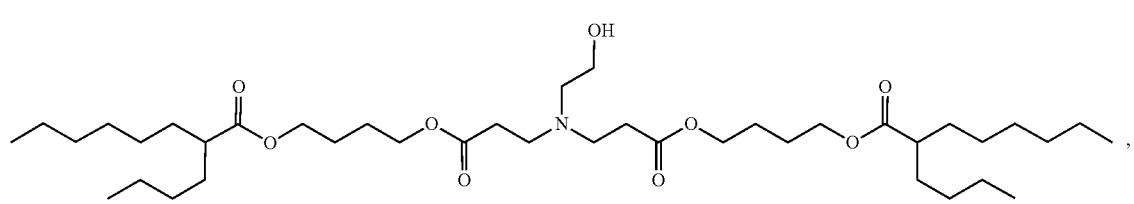

5

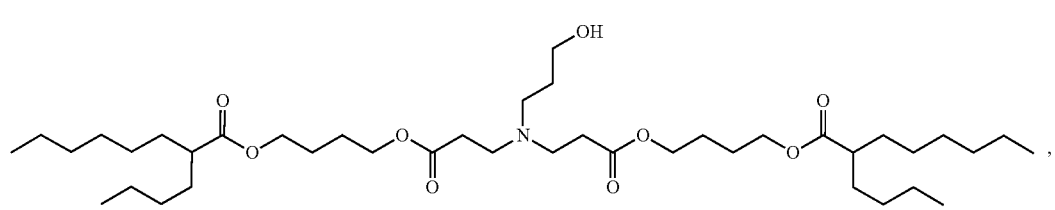

6

-continued
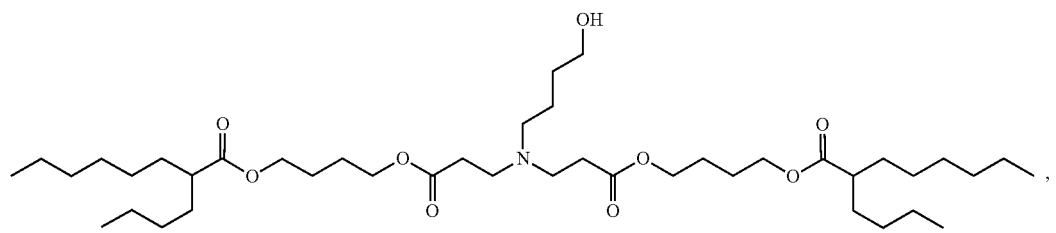
7
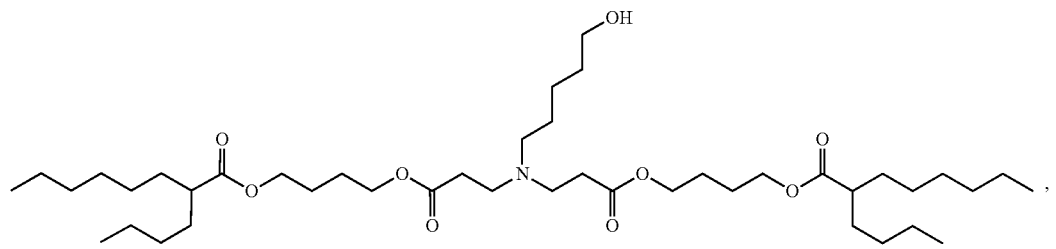
8
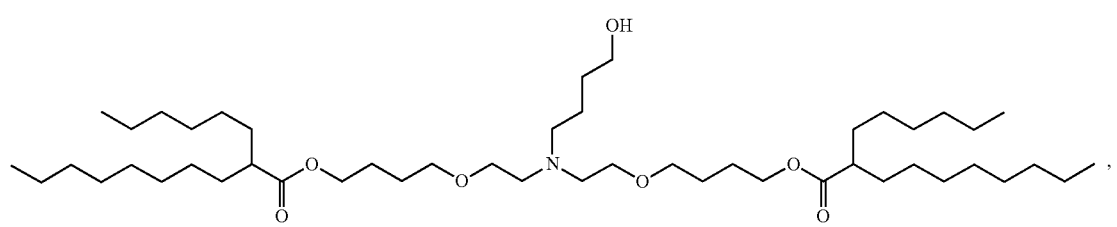
9
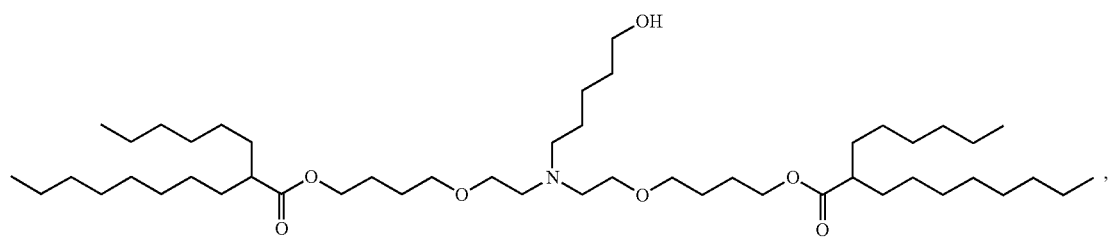
10
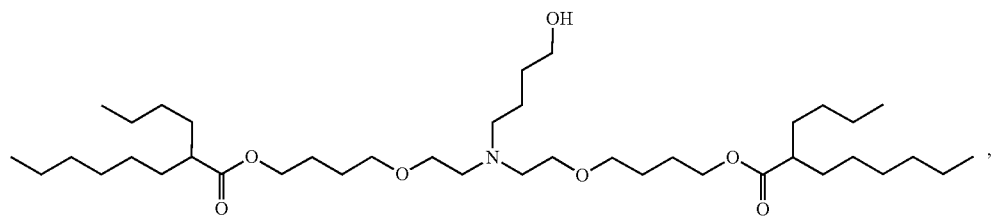
11
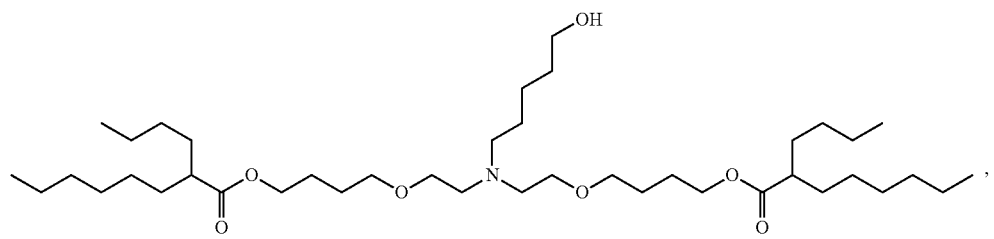
12
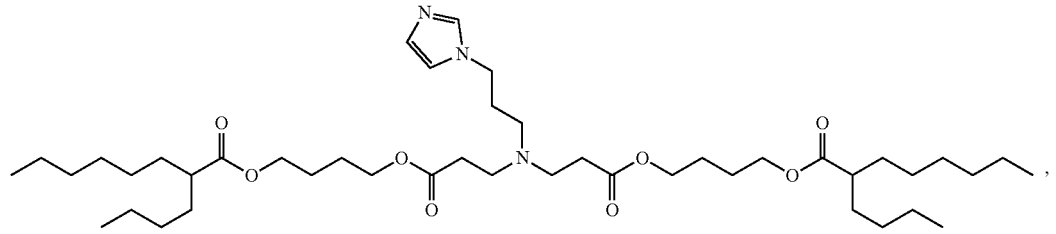
13

-continued
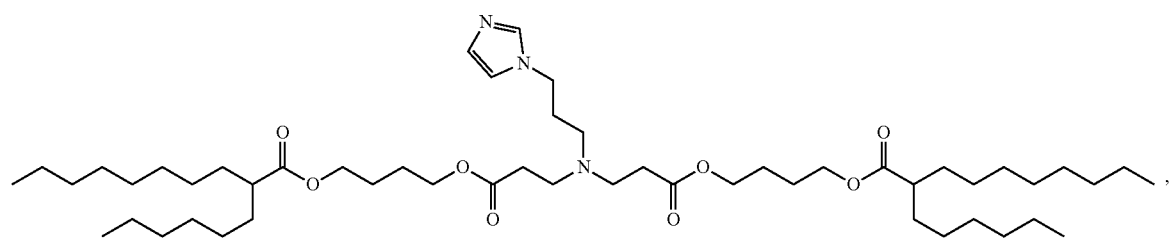
14
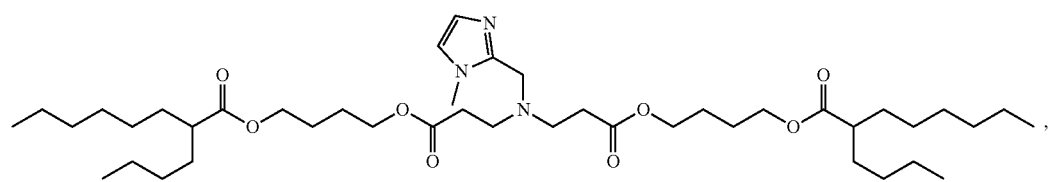
15
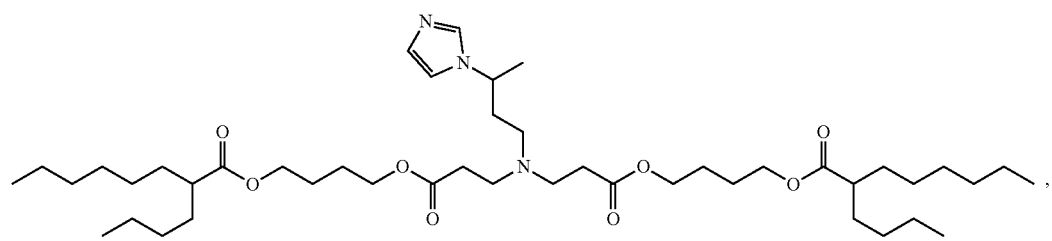
16
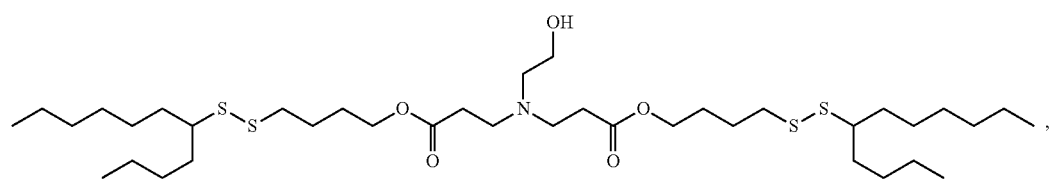
17
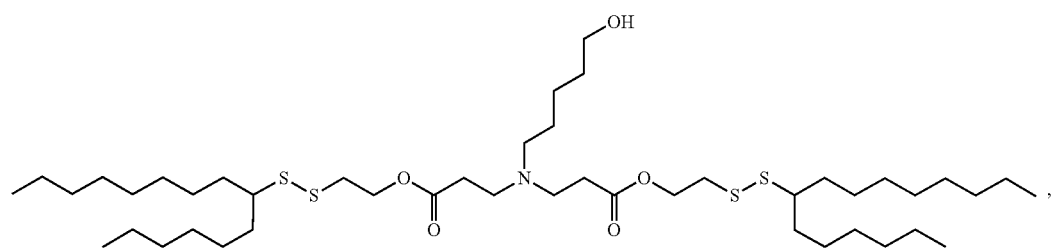
18
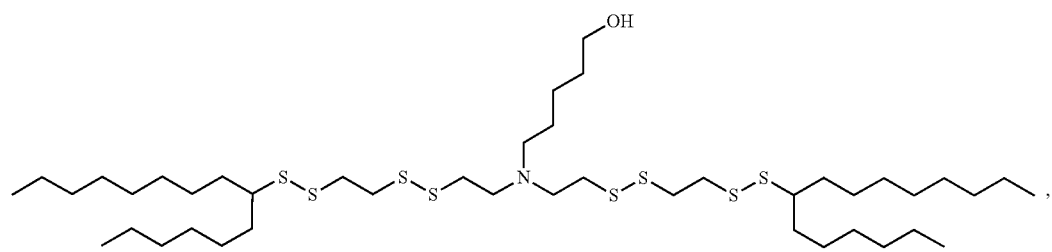
19
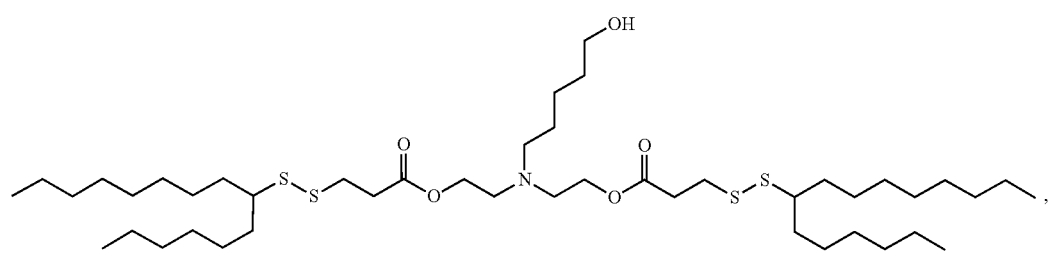
20

-continued
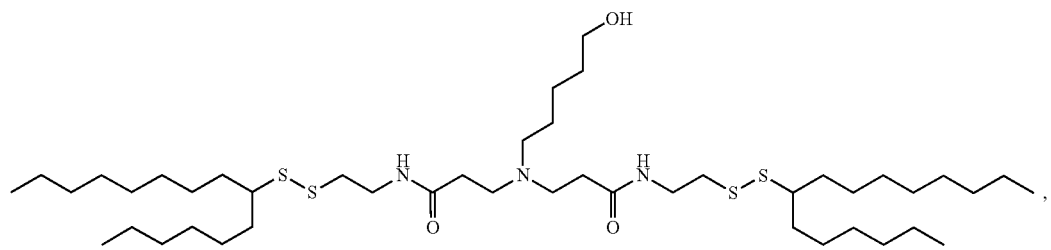
21
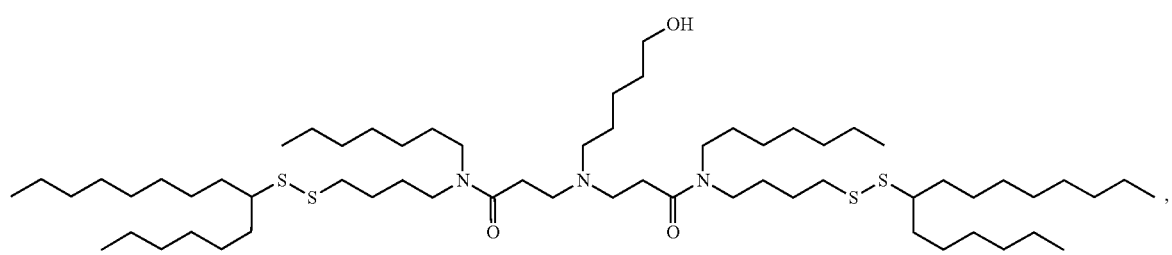
22
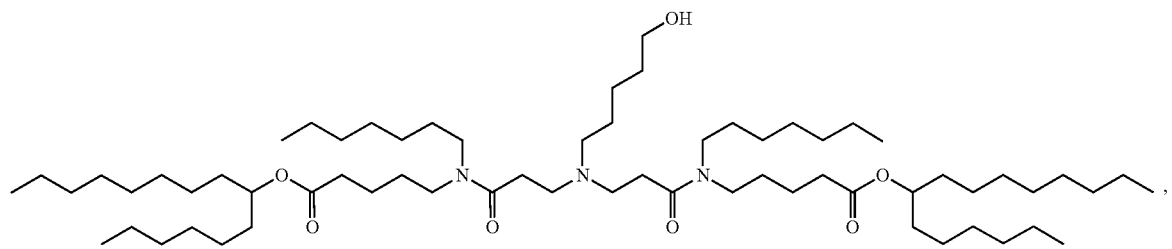
23
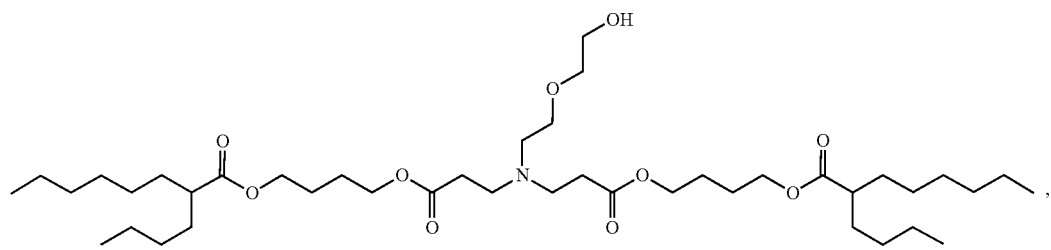
24
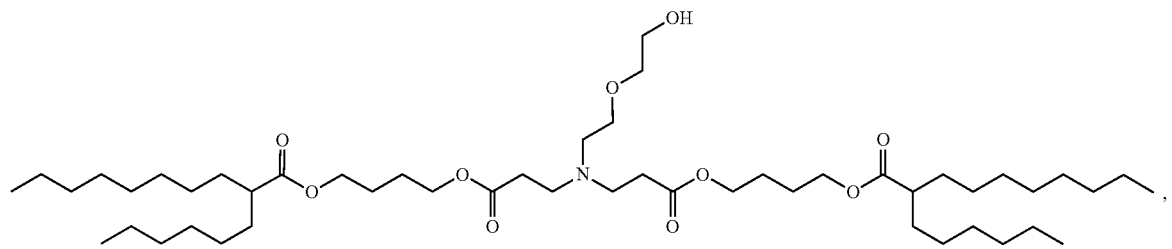
25
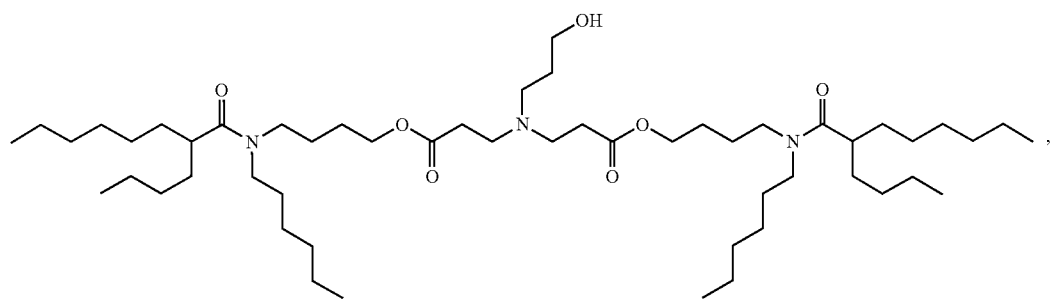
26

27
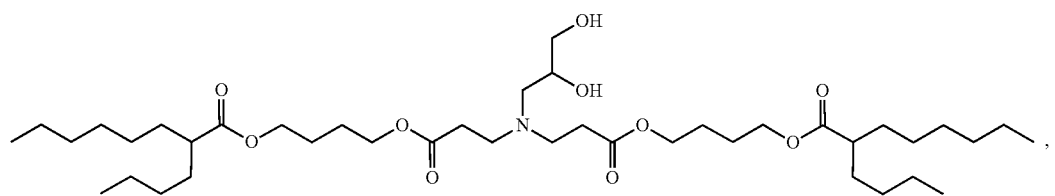
28
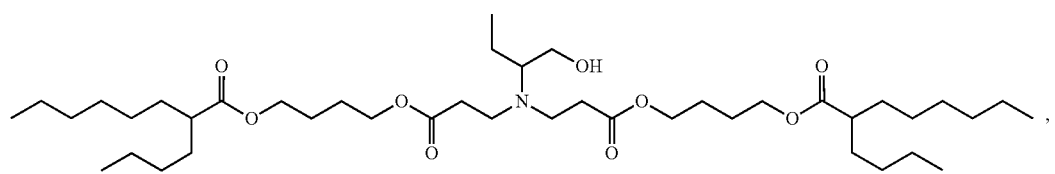
29
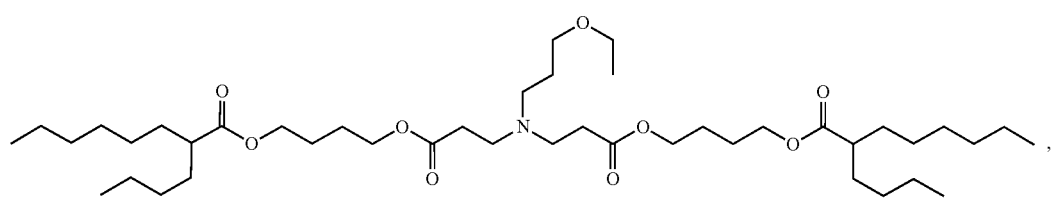
30
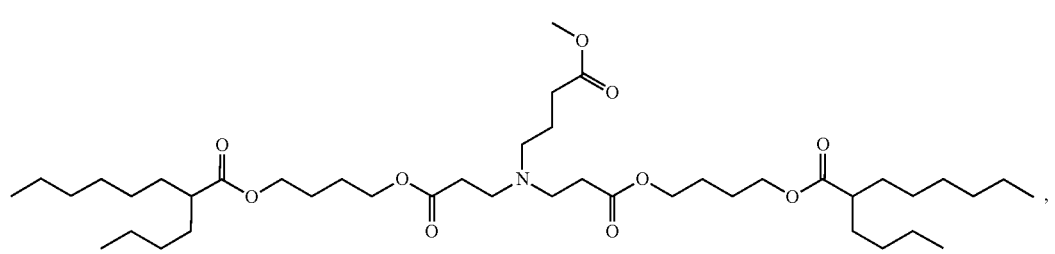
31
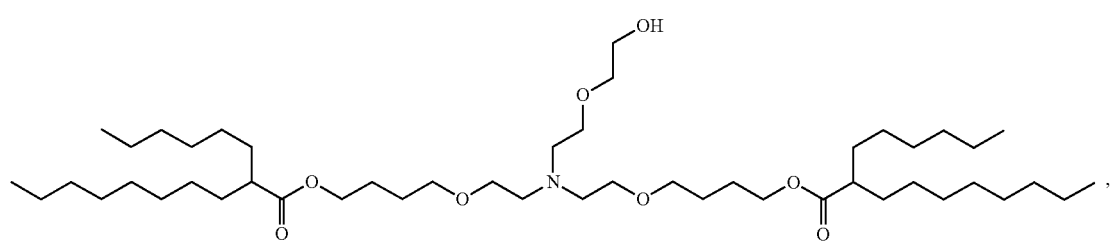
32
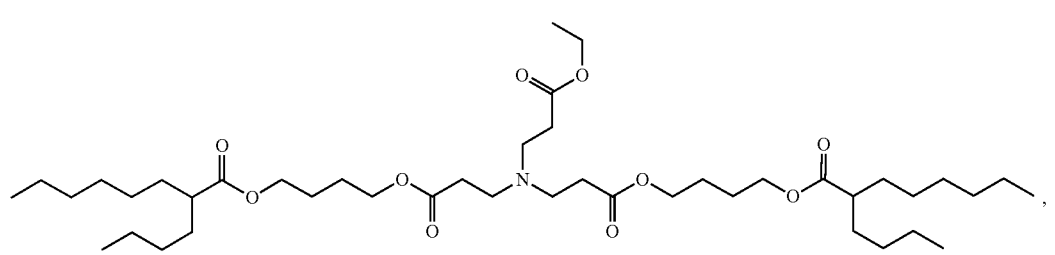
33
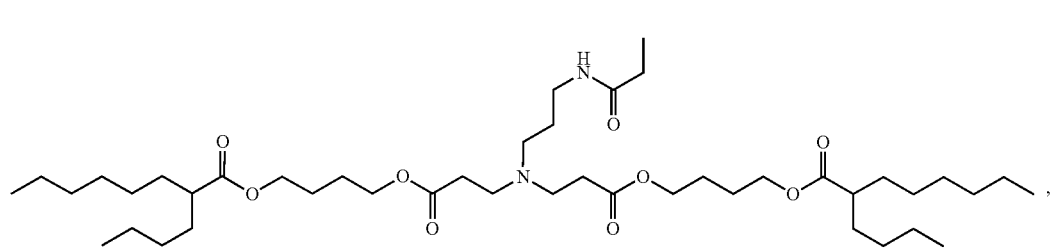

-continued
34
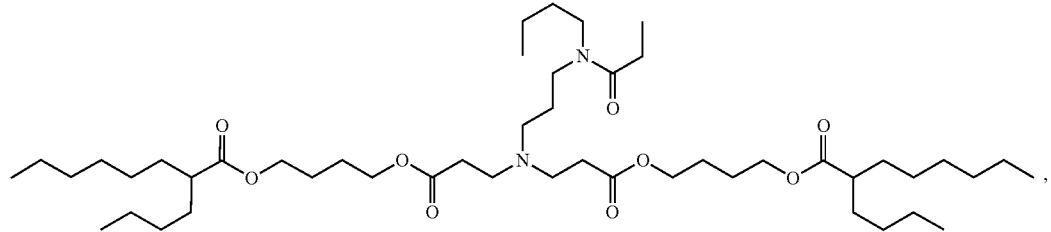,
35
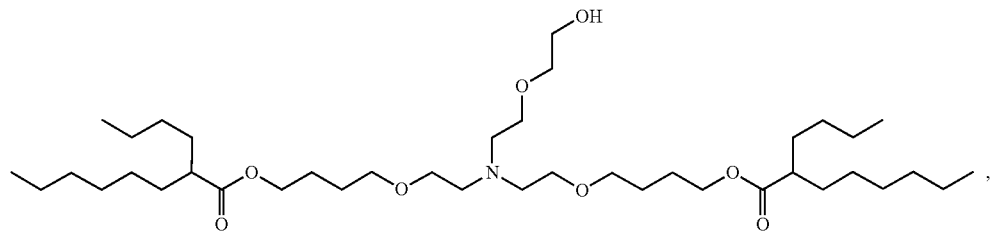,
36
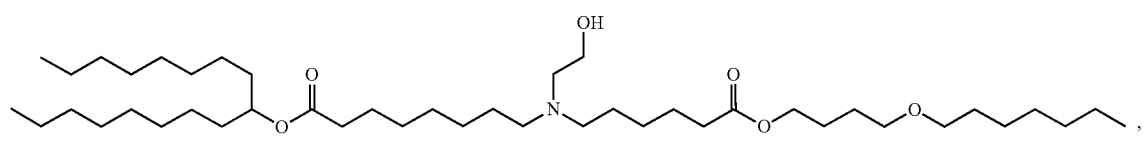,
37
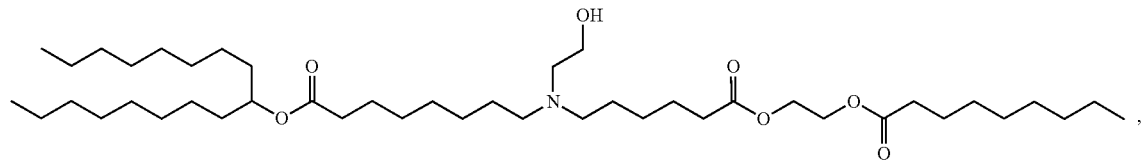,
38
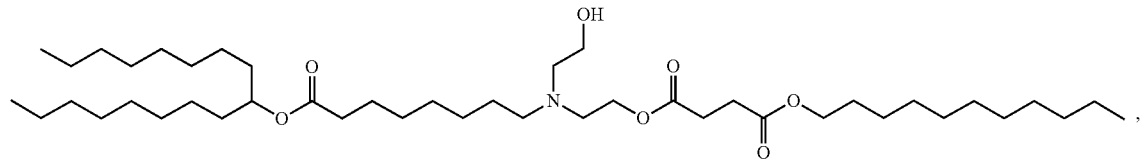,
39
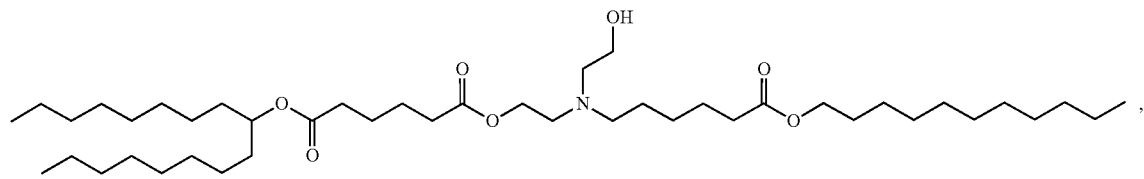,
40
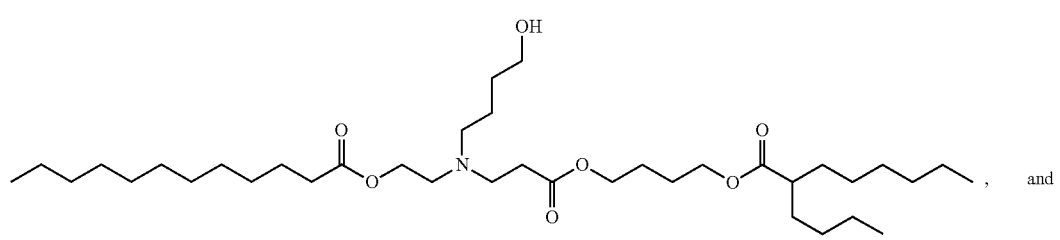, and
41
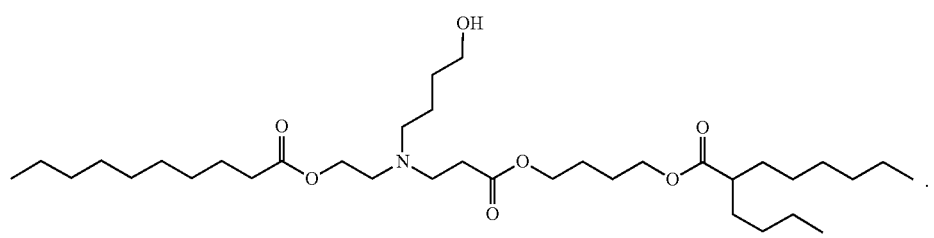.

<A Third Aspect>

The present invention provides a lipid carrier, including the compound or the pharmaceutically acceptable salt, stereoisomer, tautomer, solvate, chelate, non-covalent complex or prodrug thereof according to <the first aspect>, and <the second aspect>;

preferably, the lipid carrier includes a first lipid compound and a second lipid compound, wherein, the first lipid compound includes the compound or the pharmaceutically acceptable salt, stereoisomer, tautomer, solvate, chelate, non-covalent complex or prodrug thereof according to <the first aspect>, and <the second aspect> as well as cationic lipid, and the second lipid compound includes one or a combination of two or more of anionic lipid, neutral lipid, sterol and amphiphilic lipid;

preferably, the cationic lipid includes one or a combination of two or more of DLinDMA, DODMA, DLin-MC2-MPZ, DLin-KC2-DMA, DOTAP, C12-200, DC-Chol and DOTMA;

the anionic lipid includes one or a combination of two or more of phosphatidyl serine, phosphatidyl inositol, phosphatidic acid, phosphatidyl glycerol, DOPG, DOPS and dimyristoyl phosphatidylglycerol;

the neutral lipid includes at least one of DOPE, DSPC, DPPC, DOPC, DPPG, POPC, POPE, DPPE, DMPE, DSPE, and SOPE or its lipid modified by an anionic or cationic modifying group;

the amphiphilic lipid includes one or a combination of two or more of PEG-DMG, PEG-c-DMG, PEG-C14, PEG-c-DMA, PEG-DSPE, PEG-PE, PEG-modified ceramide, PEG-modified dialkylamine, PEG-modified diacylglycerol, Tween-20, Tween-80, PEG-DPG, PEG-s-DMG, DAA, PEG-c-DOMG and GalNAc-PEG-DSG;

preferably, in the lipid carrier, a molar ratio of the first lipid compound to the anionic lipid the neutral lipid to the sterol to the amphiphilic lipid is (20-65):(0-20):(5-25):(25-55):(0.3-15);

wherein, in the first lipid compound, a molar ratio of the compound of the formula (I) or the pharmaceutically acceptable salt, stereoisomer, tautomer, solvate, chelate, non-covalent complex or prodrug thereof according to <the first aspect>, and <the second aspect> to said cationic lipid is (1-10):(0-10).

<A Fourth Aspect>

The present invention provides a nucleic acid lipid nanoparticle composition, including the compound or the pharmaceutically acceptable salt, stereoisomer, tautomer, solvate, chelate, non-covalent complex or prodrug thereof according to <the first aspect>, and <the second aspect> or the lipid carrier according to <the third aspect>, as well as a nucleic acid drug;

preferably, the nucleic acid drug includes one or a combination of two or more of DNA, siRNA, mRNA, dsRNA, antisense nucleic acid, microRNA, antisense microRNA, antagomir, a microRNA inhibitor, a microRNA activator and immunostimulatory nucleic acid;

preferably, a mass ratio of the nucleic acid drug to the compound or the pharmaceutically acceptable salt, stereoisomer, tautomer, solvate, chelate, non-covalent complex or prodrug thereof according to <the first aspect>, and <the second aspect> is 1:(3-40); or, a mass ratio of the nucleic acid drug to the lipid carrier according to <the third aspect> is 1:(3-40).

<A Fifth Aspect>

The present invention provides a pharmaceutical preparation, including the compound or the pharmaceutically acceptable salt, stereoisomer, tautomer, solvate, chelate, non-covalent complex or prodrug thereof according to <the first aspect>, and <the second aspect>, or the lipid carrier according to <the third aspect>, or the nucleic acid lipid nanoparticle composition according to <the fourth aspect>, as well as a pharmaceutically acceptable excipient, carrier and diluent agent;

preferably, the pharmaceutical preparation has a particle size of 30-500 nm;

preferably, the entrapment efficiency of the nucleic acid drug in the pharmaceutical preparation is greater than 50%.

Effect of the Invention

The present invention provides a series of compounds of the formula (I) having a novel structure, the compounds can be used as cationic lipid for preparing a lipid carrier together with other lipid compounds, are controllable, uniformly distributed, and monodisperse in particle size, and have a high entrapment efficiency to drugs with a negative charge. And, the compounds can exhibit different electric potentials under different pHs, when drugs with a negative charge are entrapped under an acidic condition the compounds exhibit a positive electricity, so that a positively charged lipid carrier and negatively charged drugs attract each other; the compounds can also exhibit electroneutrality or electronegativity in vivo i.e. under a neutral condition, so as to avoid causing great cytotoxicity. Furthermore, a lipid compound with a specific structure can be chosen as a lipid carrier based on an organ in which the nucleic acid drug needs to be enriched.

Further, a synthetic route of the compound is simple, and the raw materials are cheap and readily available, having a high market potential.

DETAILED DESCRIPTION

Figure 1:
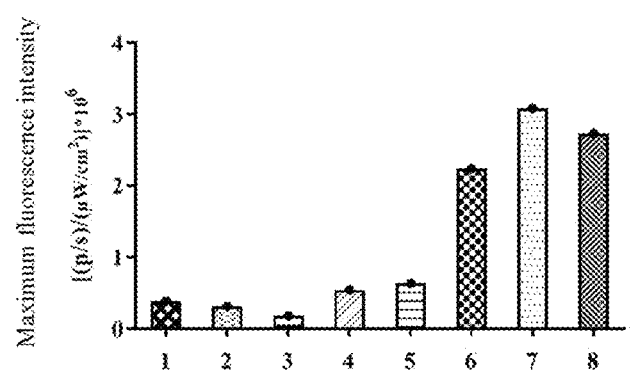
FIG. 1 is a comparison diagram of maximum fluorescence of intramuscular injection of LNP@mRNAs jointly prepared from compounds 1-8 in Example 25 and other three lipids.

In prior to further description of the present invention, it should be understood that the present invention is not limited to the specific embodiments described herein; it should also be understood that the terms used herein are only for purpose of description and not limiting the specific embodiments.

Definition of Terms

Unless otherwise noted, the meanings of the following terms are as follow:

The term "pharmaceutically acceptable salt" refers to a salt of the compound of the present invention which is essentially non-toxic to organisms. The pharmaceutically acceptable salt generally includes (but is not limited to) a salt formed by a reaction of the compound of the present invention with a pharmaceutically acceptable inorganic/organic acid or inorganic/organic base, and such salt is also known as an acid addition salt or an alkali addition salt. Common inorganic acids include (but are not limited to) hydrochloric acid, hydrobromic acid, sulfuric acid, phosphoric acid, etc., and common organic acids include (but are not limited to) trifluoroacetic acid, citric acid, maleic acid, fumaric acid, succinic acid, tartaric acid, lactic acid, pyruvic acid, oxalic acid, formic acid, acetic acid, benzoic acid, methanesulfonic acid, benzenesulfonic acid, p-toluenesulfonic acid, etc., common inorganic bases include (but are not limited to) sodium hydroxide, potassium hydroxide, calcium hydroxide, barium hydroxide, etc., and common organic bases include (but are not limited to) diethylamine, triethylamine, ethambutol, etc.

The term "stereoisomer" (also known as "an optical isomer") refers to a stable isomer that has a vertical asymmetric plane due to at least one chirality element (including a chiral center, a chiral axis, a chiral plane, etc.), which enables plane polarized light to rotate. Because in the compounds of the present invention, there are asymmetric centers and other chemical structures which may result in stereoisomerism, the present invention also includes these stereoisomers and a mixture thereof. Because the compounds and salts thereof of the present invention include asymmetric carbon atoms, they can exist in the form of a single stereoisomer, a racemate, or a mixture of enantiomer and diastereoisomer. Generally, these compounds can be prepared in the form of a racemic mixture. However, if necessary, such compounds can be prepared or separated to obtain a pure stereoisomer, i.e. a single enantiomer or diastereoisomer, or a mixture of enriched single stereoisomer (a purity of ≥98%, ≥95%, ≥93%, ≥90%, ≥88%, ≥85% or ≥80%). The single stereoisomer of the compound is prepared from an optically active starting material containing a required chiral center, or obtained by preparing a mixture of enantiomer products, followed by separation or resolution, for example, conversion into a mixture of diastereoisomers, followed by separation or recrystallization, chromatographic treatment, using a chiral resolving agent, or direct separation of enantiomers on a chiral chromatographic column. A starting compound having specific stereochemistry can be either commercially available, or can be obtained by preparation in accordance with a method described hereinafter, followed by resolution by a method well-known in the art.

The term "tautomer" (also known as "a tautomeric form") refers to structural isomers having different energies which can be mutually transformed through a low-energy barrier. If a tautomerism is possible (such as in a solution), then a chemical equilibrium of tautomers can be achieved. For example, a proton tautomer (also known as a proton transfer tautomer) includes (but is not limited to) mutual transformation which is conducted by proton transfer, such as keto-enol isomerization, imine-enamine isomerization, amide-imidohydrine isomerization, etc. Unless otherwise noted, all tautomer forms of the compound of the present invention are all within the scope of the present invention.

The term "solvate" refers to a substance formed by binding of the compound or the pharmaceutically acceptable salt thereof of the present invention with at least one solvent molecule through a non-covalent intermolecular force. Common solvates include (but are not limited to) a hydrate, an ethanolate, an acetonide, etc.

The term "chelate" refers to a complex having a cyclic structure, and is obtained by chelation of two or more ligands with a same metal ion to form a chelate ring.

The term "non-covalent complex" is formed by interaction of a compound with another molecule, wherein a covalent bond is not formed between the compound and the molecule. For example, complex can occur by Van der Waals interaction, hydrogen bonding and electrostatic interaction (also known as ionic bonding).

The term "prodrug" refers to a derived compound which is able to directly or indirectly provide the compound of the present invention after being administered to a patient. A particularly preferred derived compound or prodrug is a compound which can enhance bioavailability of the compound of the present invention (for example, easier absorption into blood), or a compound which promotes delivery of a parent compound to an action site (e.g., a lymphatic system) when being administered to the patient. Unless otherwise noted, all prodrug forms of the compound of the present invention are all within the scope of the present invention, and various prodrug forms are well known in the art.

The term "each independently" means that at least two groups (or ring systems) with a same or similar value range in a structure can have same or different meanings under specific circumstances. For example, a substituent X and a substituent Y are each independently hydrogen, halogen, hydroxyl, cyano, alkyl or aryl, when the substituent X is hydrogen, the substituent Y can be either hydrogen, or be halogen, hydroxyl, cyano, alkyl or aryl; similarly, when the substituent Y is hydrogen, the substituent X can either be hydrogen, or be halogen, hydroxyl, cyano, alkyl or aryl.

The term "optional" or "optionally" means that an event or situation described later might occur or might not occur, and the description includes occurrence of said event or situation and nonoccurrence of said event or situation.

The terms "include" and "comprise" are used in an open and non-restrictive meaning thereof.

The term "alkyl" refers to a saturated linear or branched hydrocarbon chain free radical which consists of only carbon and hydrogen atoms, including (but not limited to) methyl, ethyl, propyl, isopropyl, butyl, sec-butyl, isobutyl and tert-butyl, etc. For example, "$C_{1-24}$ alkyl" refers to saturated linear or branched alkyl containing 1 to 24 carbon atoms.

The term "alkylene" refers to a bidentate free radical which is obtained by removing a hydrogen atom from the alkyl as defined above, including (but not limited to) methylene, 1,1-ethylene and 1,2-ethylene, etc. For example, "$C_{1-24}$ alkylene" refers to a bidentate free radical obtained by removing a hydrogen atom from linear or branched alkyl containing 1 to 24 carbon atoms.

The term "cycloalkyl" refers to a saturated monocyclic, dicyclic, tricyclic or tetracyclic free radical, and can be condensed, bridged or spirocyclic, including (but not limited to) cylcopropyl, cylcobutyl, cyclopentyl, cyclopentenyl, cyclohexyl, cycloheptyl and adamantyl, etc.

The term "cycloalkylene" refers to a bidentate free radical which is obtained by removing a hydrogen atom from the cycloalkyl as defined above, including (but not limited to) cyclopropylene, cyclobutylene, cyclopentylene, cyclopentenylene, cyclohexylene and cycloheptylene, etc. For example, "$C_{3-24}$ cycloalkylene" refers to a bidentate free radical which is obtained by removing a hydrogen atom from cycloalkyl containing 3 to 24 carbon atoms.

The term "branched alkyl" refers to a saturated hydrocarbon chain free radical which is connected with a parent molecule via a non-terminal carbon atom.

The term "alkenyl" refers to an unsaturated linear or branched hydrocarbon chain free radical which consists of only carbon and hydrogen atoms, including (but not limited to) groups such as vinyl, propenyl, allyl, isopropenyl, butenyl and isobutenyl, etc. For example, "$C_{2-24}$ alkenyl" refers to linear or branched alkyl containing 2 to 24 carbon atoms and having at least one unsaturated site (>C=C<).

The term "alkenylene" refers to a bidentate free radical which is obtained by removing a hydrogen atom from the alkenyl as defined above, including (but not limited to) vinylidene, etc. For example, "$C_{2-24}$ alkenylene" refers to a bidentate free radical which is obtained by removing a hydrogen atom from linear or branched alkenyl containing 2 to 24 carbon atoms.

The term "cycloalkenyl" refers to unsaturated monocyclic, bicyclic, tricyclic or tetracyclic free radical, the cycloalkenyl can be condensed, bridged or spirocyclic, including (but not limited to) cyclopropenyl and cyclobutenyl, etc.

The term "cycloalkenylene" refers to a bidentate free radical which is obtained by removing a hydrogen atom from the cycloalkenyl as define above, including (but not limited to) cyclopropenylene and cyclobutenylene, etc. For example, "$C_{3-24}$ cycloalkenylene" refers to a bidentate free radical which is obtained by removing a hydrogen atom from cycloalkenyl containing 3 to 24 carbon atoms.

The term "branched alkenyl" refers to an unsaturated hydrocarbon chain free radical which is connected with a parent molecule via a non-terminal carbon atom.

The term "heterocyclyl" refers to a monocyclic, bicyclic, tricyclic or tetracyclic free radical, and it has carbon atoms and at least one heteroatom in a ring system, and may include condensed, bridged or spirocyclic system. For example, 5- to 7-membered heterocyclyl refers to saturated or partially unsaturated monocyclic or polycyclic heterocyclyl containing 5 to 7 carbon atoms and heteroatoms or heteroatom groups for ring-forming.

Compound of a General Formula

The present invention provides a compound of a formula (I) or a pharmaceutically acceptable salt, stereoisomer, tautomer, solvate, chelate, non-covalent complex or prodrug thereof,

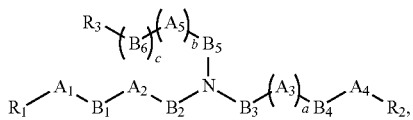

wherein:
$A_1$, $A_2$, $A_3$, $A_4$ and $A_5$ are each independently one or more of —O(C=O)—, —(C=O)O—, —C(=O)—, —O—, —S(O)—, —S—S—, —C(=O)S—, —SC(=O)—, —NR$^a$C(=O)—, —C(=O)NR$^a$—, —NR$^a$OC(=O)—, —OC(=O)NR$^a$— or —NR$^a$OC(=O)NR$^a$—;

$B_1$, $B_2$, $B_3$ and $B_4$ are each independently CI-12 alkylene or $C_{2-12}$ alkenylene;

$B_5$ and $B_6$ are each independently $C_{1-24}$ alkylene, $C_{2-24}$ alkenylene, $C_{3-24}$ cycloalkylene or $C_{3-24}$ cycloalkenylene;

$R_1$ and $R_2$ are each independently $C_{1-24}$ alkyl or $C_{2-24}$ alkenyl;

$R_3$ is hydrogen, CN, hydroxyl, hydroxyl-substituted alkyl or 5- to 7-membered heterocyclyl; wherein, the 5- to 7-membered heterocyclyl is optionally substituted by $C_{1-4}$ alkyl, and contains 1 to 4 ring-forming heteroatoms, and the heteroatoms are each independently N, O or S;

$R^a$ is hydrogen or $C_{1-24}$ alkyl; and a, b and c are each independently 0 or 1.

In some specific embodiments of the present invention, $A_1$, $A_2$, $A_3$, $A_4$ and $A_5$ are each independently one of —O(C=O)—, —(C=O)O—, —O—, —S—S—, —NR$^a$C(=O)— or —C(=O)NR$^a$—. Wherein, R$^a$, $B_1$, $B_2$, $B_3$, $B_4$, $B_5$, $B_6$, $R_1$, $R_2$, $R_3$, a, b and c are as defined in the formula (I).

In some preferred embodiments of the present invention, R$^a$ is hydrogen or $C_{1-24}$ hydrocarbyl, more preferably hydrogen or $C_{1-24}$ alkyl, further preferably hydrogen or $C_{1-8}$ alkyl. Particularly, R$^a$ can be hydrogen, methyl, ethyl, propyl, butyl, pentyl, hexyl, heptyl, octyl and possible isomers thereof, more particularly, R$^a$ can be hydrogen, n-butyl, n-hexyl or n-heptyl.

In some preferred embodiments of the present invention, $B_1$, $B_2$, $B_3$ and $B_4$ are each independently $C_{1-12}$ alkylene or $C_{2-12}$ alkenylene, more preferably $C_{1-8}$ alkylene or $C_{2-8}$ alkenylene, more preferably $C_{1-8}$ alkylene. Particularly, $B_1$, $B_2$, $B_3$ and $B_4$ are each independently —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$— or —CH$_2$CH$_2$CH$_2$CH$_2$CH$_2$CH$_2$CH$_2$—.

In some preferred embodiments of the present invention, $B_5$ and $B_6$ are each independently $C_{1-24}$ alkylene, $C_{2-24}$ alkenylene, $C_{3-24}$ cycloalkylene or $C_{3-24}$ cycloalkenylene, more preferably $C_{1-24}$ alkylene, further preferably $C_{1-8}$ alkylene, particularly $B_5$ and $B_6$ are each independently —CH$_2$—, —CH$_2$CH$_2$—, —CH$_2$CH$_2$CH$_2$—, —CH$_2$CH$_2$CH$_2$CH$_2$—, —CH$_2$CH$_2$CH(CH$_3$)—, —CH$_2$CH(CH$_2$CH$_3$)— or —CH$_2$CH$_2$CH$_2$CH$_2$CH$_2$—.

In some specific embodiments of the present invention, $R_1$ and $R_2$ are each independently $C_{1-24}$ alkyl or $C_{2-24}$ alkenyl, more preferably $C_{4-24}$ alkyl or $C_{4-24}$ alkenyl.

In some specific embodiments of the present invention, $R_3$ is hydrogen, hydroxyl, hydroxyl-substituted alkyl or 5- to 7-membered heterocyclyl; wherein, the 5- to 7-membered heterocyclyl is optionally substituted by $C_{1-4}$ alkyl, and contains 1 to 4 ring-forming heteroatoms, and the heteroatoms are each independently N, O or S.

In some preferred embodiments of the present invention, in the compound of the formula (I), a is 0, namely the compound has a structure shown in a formula (I-1):

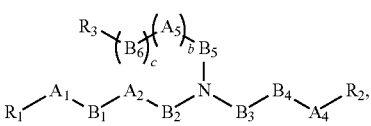

wherein, $A_1$, $A_2$, $A_4$, $A_5$, $B_1$, $B_2$, $B_3$, $B_4$, $B_5$, $B_6$, $R_1$, $R_2$, $R_3$, b and c are as defined in the formula (I).

For the above formula (I-1):

in some preferred embodiments of the present invention, $R_3$ is hydroxyl or hydroxyl-substituted alkyl.

In some more preferred embodiments of the present invention, $A_1$, $A_2$, $A_3$, $A_4$ and $A_5$ are each independently —O—, —O(C=O)— or —(C=O)O—.

In some more preferred embodiments of the present invention, b is 0 or 1, preferably 0.

In some more preferred embodiments of the present invention, $B_1$, $B_2$, $B_3$ and $B_4$ are each independently $C_{1-8}$ alkylene or $C_{2-8}$ alkenylene, further preferably $C_{1-8}$ alkylene. Particularly, $B_1$, $B_2$, $B_3$ and $B_4$ are each independently —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —CH$_2$CH$_2$CH$_2$CH$_2$CH$_2$CH$_2$.

In some more preferred embodiments of the present invention, $B_5$ and $B_6$ are each independently $C_{1-24}$ alkylene, further preferably $C_{1-8}$ alkylene, particularly $B_5$ and $B_6$ can be —CH$_2$—, —CH$_2$CH$_2$—, —CH$_2$CH$_2$CH$_2$— or —CH$_2$CH$_2$CH$_2$CH$_2$—.

In some more preferred embodiments of the present invention, c is 0 or 1.

In some more preferred embodiments of the present invention, $R_1$ and $R_2$ are each independently $C_{4-24}$ branched alkyl or $C_{4-24}$ branched alkenyl, further preferably $C_{4-12}$ branched alkyl. Particularly, $R_1$ and $R_2$ are each independently the following fragments:

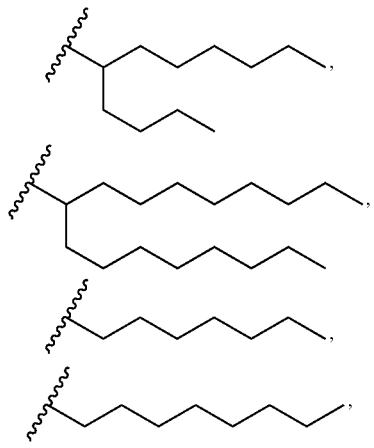

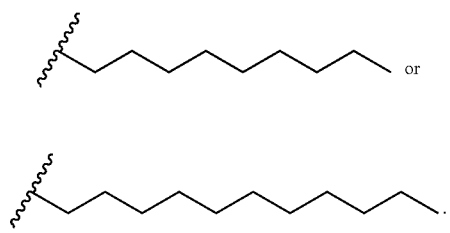

In some more preferred embodiments of the present invention, $R_3$ is hydroxyl, b and c are 0, $B_5$ is $C_{1-8}$ alkylene, particularly —CH$_2$CH$_2$—; and the remaining $A_1$, $A_2$, $A_4$, $A_5$, $B_1$, $B_2$, $B_3$, $B_4$, $B_5$, $B_6$, $R_1$ and $R_2$ are as described above.

In some preferred embodiments of the present inventions, in the compound of the formula (I), a is 1, namely the compound has a structure shown in a formula (I-2):

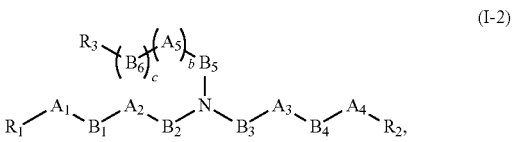

(I-2)

wherein, $A_1$, $A_2$, $A_3$, $A_4$, $A_5$, $B_1$, $B_2$, $B_3$, $B_4$, $B_5$, $B_6$, $R_1$, $R_2$, $R_3$, b and c are as defined in the formula (I).

In some more preferred embodiments of the present invention, $R_1$ and $R_2$ are each independently $C_{4-24}$ branched alkyl or $C_{4-24}$ branched alkenyl, further preferably $C_{4-18}$ branched alkyl. Particularly, $R_1$ and $R_2$ are each independently the following fragments:

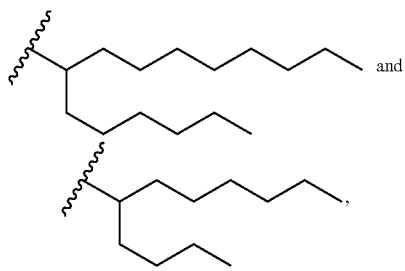

and the remaining $A_1$, $A_2$, $A_3$, $A_4$, $A_5$, $B_1$, $B_2$, $B_3$, $B_4$, $B_5$, $B_6$, $R_3$, b and c are as defined in the formula (I).

For the above formula (I-2):

$R_3$ is hydrogen, hydroxyl, hydroxyl-substituted alkyl or 5- to 7-membered heterocyclyl; wherein, the 5- to 7-membered heterocyclyl is optionally substituted by $C_{1-4}$ alkyl, and contains 1 to 4 ring-forming heteroatoms, and the heteroatoms are each independently N, O or S.

particularly:

when $R_3$ is hydroxyl or hydroxyl-substituted alkyl, $A_1$, $A_2$, $A_3$, $A_4$, $A_5$, $B_1$, $B_2$, $B_3$, $B_4$, $B_5$, $B_6$, $R_1$, $R_2$, b and c are as defined above. In this case:

in some more preferred embodiments of the present invention, the compound of the formula (I-2) has a structure shown in a formula (I-2-1):

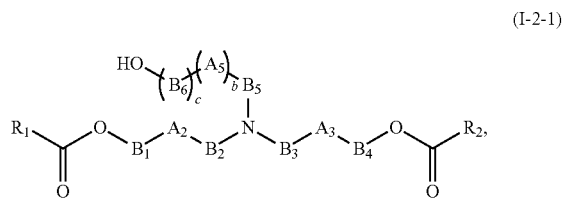

(I-2-1)

wherein, $A_2$, $A_3$, $A_5$, $B_1$, $B_2$, $B_3$, $B_4$, $B_5$, $B_6$, $R_1$, $R_2$, b and c are as defined in the formula (I-2).

For the above formula (I-2-1), in some more preferred embodiments of the present invention, $A_5$ is —O—, —O(C=O)— or —(C=O)O—, and $A_2$, $A_3$, $B_1$, $B_2$, $B_3$, $B_4$, $B_5$, $B_6$, $R_1$, $R_2$, b and c are as defined in the formula (I-2).

Further preferably, the compound of the formula (I-2-1) has a structure shown in a formula (I-2-1-1):

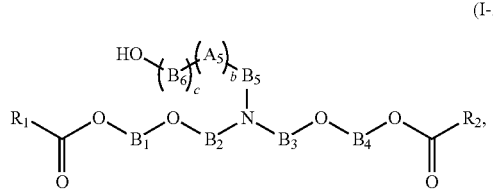
(I-2-1-1)

wherein, $A_5$, $B_1$, $B_2$, $B_3$, $B_4$, $B_5$, $B_6$, $R_1$, $R_2$, b and c are as defined in the formula (I-2-1).

For the above formula (I-2-1-1):
in some more preferred embodiments of the present invention, b is 0 or 1. When b is 1, $A_5$ is —O—.

In some more preferred embodiments of the present invention, $B_1$, $B_2$, $B_3$ and $B_4$ are each independently $C_{1-8}$ alkylene or $C_{2-8}$ alkenylene, further preferably $C_{1-4}$ alkylene. Particularly, $B_1$ and $B_4$ are each independently —CH$_2$CH$_2$CH$_2$CH$_2$—, and $B_2$ and $B_3$ are each independently —CH$_2$CH$_2$—.

In some more preferred embodiments of the present invention, $B_5$ and $B_6$ are each independently $C_{1-24}$ alkylene, further preferably $C_{1-8}$ alkylene, particularly $B_5$ and $B_6$ can be —CH$_2$—, —CH$_2$CH$_2$—, —CH$_2$CH$_2$CH$_2$—, —CH$_2$CH$_2$CH$_2$CH$_2$— or —CH$_2$CH$_2$CH$_2$CH$_2$CH$_2$—.

In some more preferred embodiments of the present invention, c is 0 or 1.

In some more preferred embodiments of the present invention, $R_1$ and $R_2$ are each independently $C_{4-24}$ branched alkyl or $C_{4-24}$ branched alkenyl, further preferably $C_{4-18}$ branched alkyl. Particularly, $R_1$ and $R_2$ are each independently the following fragments:

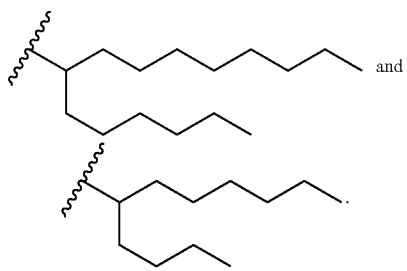

Or, the compound of the formula (I-2-1) has a structure shown in a formula (I-2-1-2):

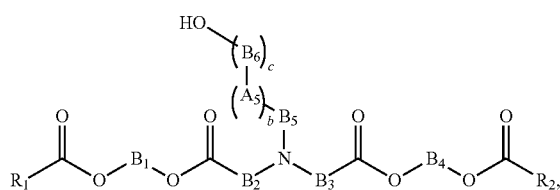
(I-2-1-2)

wherein, $A_5$, $B_1$, $B_2$, $B_3$, $B_4$, $B_5$, $B_6$, $R_1$, $R_2$, b and c are as defined in the formula (I-2-1).

For the above formula (I-2-1-2):
in some more preferred embodiments of the present invention, b is 0 or 1. When b is 1, $A_5$ is —O—.

In some more preferred embodiments of the present invention, $B_1$, $B_2$, $B_3$ and $B_4$ are each independently $C_{1-8}$ alkylene or $C_{2-8}$ alkenylene, further preferably $C_{1-4}$ alkylene. Particularly, $B_1$ and $B_4$ are each independently —CH$_2$CH$_2$CH$_2$CH$_2$—, and $B_2$ and $B_3$ are each independently —CH$_2$CH$_2$—.

In some more preferred embodiments of the present invention, $B_5$ and $B_6$ are each independently $C_{1-24}$ alkylene, further preferably $C_{1-8}$ alkylene, particularly $B_5$ and $B_6$ can be —CH$_2$—, —CH$_2$CH$_2$—, —CH$_2$CH$_2$CH$_2$—, —CH$_2$CH$_2$CH$_2$CH$_2$—, —CH$_2$CH(CH$_2$CH$_3$)— or —CH$_2$CH$_2$CH$_2$CH$_2$CH$_2$—.

In some more preferred embodiments of the present invention, c is 0 or 1.

In some more preferred embodiments of the present invention, $R_1$ and $R_2$ are each independently $C_{4-24}$ branched alkyl or $C_{4-24}$ branched alkenyl, further preferably $C_{4-18}$ branched alkyl. Particularly, $R_1$ and $R_2$ are each independently the following fragment:

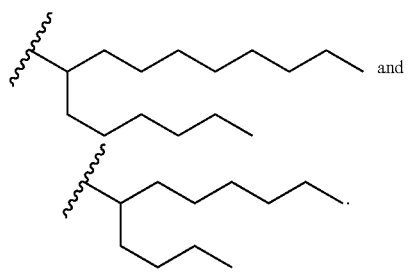

In some more preferred embodiments of the present invention, the compound of the formula (I-2) has a structure shown in a formula (I-2-2):

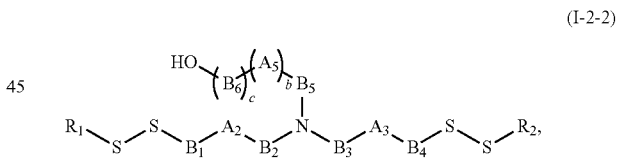
(I-2-2)

wherein, $A_2$, $A_3$, $A_5$, $B_1$, $B_2$, $B_3$, $B_4$, $B_5$, $B_6$, $R_1$, $R_2$, b and c are as defined in the formula (I-2).

For the above formula (I-2-2):
in some more preferred embodiments of the present invention, $A_2$ and $A_3$ are each independently —O(C=O)—, —(C=O)O—, —S—S—, —NR$^a$C(=O)— or —C(=O)NR$^a$—. Wherein, $R^a$ is hydrogen or $C_{1-8}$ alkyl, preferably, $R^a$ is hydrogen or n-heptyl.

In some more preferred embodiments of the present invention, $A_5$ is —O—, —O(C=O)— or —(C=O)O—.

In some more preferred embodiments of the present invention, b is 0.

In some more preferred embodiments of the present invention, $B_1$, $B_2$, $B_3$ and $B_4$ are each independently $C_{1-8}$ alkylene or $C_{2-8}$ alkenylene, further preferably $C_{1-4}$ alkylene. Particularly, $B_1$ and $B_4$ are each independently —CH$_2$CH$_2$— or —CH$_2$CH$_2$CH$_2$CH$_2$—, and $B_2$ and $B_3$ are each independently —CH$_2$CH$_2$—.

In some more preferred embodiments of the present invention, $B_5$ and $B_6$ are each independently $C_{1-24}$ alkylene, further preferably $C_{1-8}$ alkylene, particularly, $B_5$ and $B_6$ are each independently —$CH_2$—, —$CH_2CH_2$—, —$CH_2CH_2CH_2$—, —$CH_2CH_2CH_2CH_2$— or —$CH_2CH_2CH_2CH_2CH_2$—.

In some more preferred embodiments of the present invention, c is 0 or 1.

In some more preferred embodiments of the present invention, $R_1$ and $R_2$ are each independently $C_{4-24}$ branched alkyl or $C_{4-24}$ branched alkenyl, further preferably $C_{4-18}$ branched alkyl. Particularly, $R_1$ and $R_2$ are each independently the following fragments:

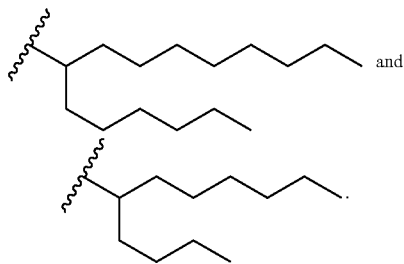

When $R_3$ is optionally substituted 5- to 7-membered heterocyclyl, the 5- to 7-membered heterocyclyl contains 1 to 4 ring-forming heteroatoms, the heteroatoms are each independently N, O or S, the substituent is $C_{1-4}$ alkyl, and $A_1$, $A_2$, $A_3$, $A_4$, $A_5$, $B_1$, $B_2$, $B_3$, $B_4$, $B_5$, $B_6$, $R_1$, $R_2$, b and c are as defined above.

In some more preferred embodiments of the present invention, the compound of the formula (I-2) has a structure shown in a formula (I-2-3):

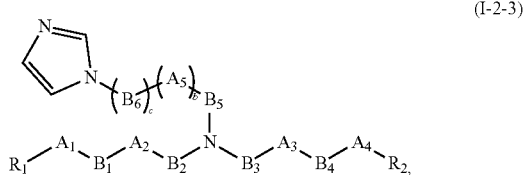

(I-2-3)

wherein, $A_1$, $A_2$, $A_3$, $A_4$, $A_5$, $B_1$, $B_2$, $B_3$, $B_4$, $B_5$, $B_6$, $R_1$, $R_2$, b and c are as defined in the formula (I-2).

For the above formula (I-2-3):
in some more preferred embodiments of the present invention, $A_5$ is —O—, —O(C=O)— or —(C=O)O—, and $A_1$, $A_2$, $A_3$, $A_4$, $B_1$, $B_2$, $B_3$, $B_4$, $B_5$, $B_6$, $R_1$, $R_2$, b and c are as defined in the formula (I-2).

Further preferably, the compound of the formula (I-2-3) has a structure shown in a formula (I-2-3-1):

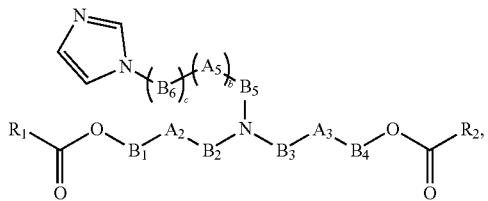

(I-2-3-1)

wherein, $A_2$, $A_3$, $A_5$, $B_1$, $B_2$, $B_3$, $B_4$, $B_5$, $B_6$, $R_1$, $R_2$, b and c are as defined in the formula (I-2-3).

For the above formula (I-2-3-1):
in some more preferred embodiments of the present invention, $A_2$ and $A_3$ are each independently —O(C=O)— or —(C=O)O—.

In some more preferred embodiments of the present invention, $B_1$, $B_2$, $B_3$ and $B_4$ are each independently $C_{1-8}$ alkylene or $C_{2-8}$ alkenylene, further preferably $C_{1-4}$ alkylene. Particularly, $B_1$ and $B_4$ are each independently —$CH_2CH_2CH_2CH_2$—, and $B_2$ and $B_3$ are each independently —$CH_2CH_2$—.

In some more preferred embodiments of the present invention, $B_5$ and $B_6$ are each independently $C_{1-24}$ alkylene, further preferably $C_{1-8}$ alkylene, particularly, $B_5$ and $B_6$ are each independently —$CH_2$—, —$CH_2CH_2$—, —$CH_2CH_2CH_2$— or —$CH_2CH_2CH(CH_3)$—.

In some more preferred embodiments of the present invention, b and c are each independently 0 or 1. Preferably, b is 0, and c is 0 or 1.

In some more preferred embodiments of the present invention, $R_1$ and $R_2$ are each independently $C_{4-24}$ branched alkyl or $C_{4-24}$ branched alkenyl, further preferably $C_{4-18}$ branched alkyl. Particularly, $R_1$ and $R_2$ are each independently the following fragments:

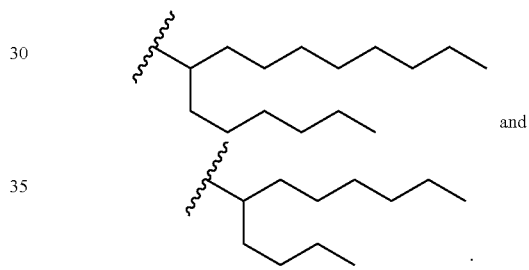

When $R_3$ is hydrogen and b is 1, $A_1$, $A_2$, $A_3$, $A_4$, $A_5$, $B_1$, $B_2$, $B_3$, $B_4$, $B_5$, $B_6$, $R_1$, $R_2$, b and c are as defined above.

In some more preferred embodiments of the present invention, the compound of the formula (I-2) has a structure shown in a formula (I-2-4):

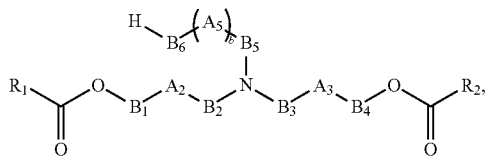

(I-2-4)

wherein, $A_2$, $A_3$, $A_5$, $B_1$, $B_2$, $B_3$, $B_4$, $B_5$, $B_6$, $R_1$, $R_2$ and b are as defined in the formula (I-2).

For the above formula (I-2-4):
in some more preferred embodiments of the present invention, $A_2$ and $A_3$ are each independently —O(C=O)— or —(C=O)O—.

In some more preferred embodiments of the present invention, $A_5$ is —O(C=O)—, —(C=O)O—, —O—, —$NR^aC(=O)$— and —$C(=O)NR^a$—, wherein, $R^a$ is as defined in the formula (I-2).

In some preferred embodiments of the present invention, $R^a$ is hydrogen or n-butyl.

In some more preferred embodiments of the present invention, $B_1$, $B_2$, $B_3$ and $B_4$ are each independently $C_{1-8}$ alkylene or $C_{2-8}$ alkenylene, further preferably $C_{1-4}$ alkylene. Particularly, $B_1$ and $B_4$ are each independently —CH$_2$CH$_2$CH$_2$CH$_2$—, and $B_2$ and $B_3$ are each independently —CH$_2$CH$_2$—.

In some more preferred embodiments of the present invention, $B_5$ and $B_6$ are each independently $C_{1-24}$ alkylene, further preferably $C_{1-8}$ alkylene, particularly, $B_5$ and $B_6$ are each independently —CH$_2$—, —CH$_2$CH$_2$— or —CH$_2$CH$_2$CH$_2$—.

In some more preferred embodiments of the present invention, b is 0 or 1. Preferably, b is 1.

In some more preferred embodiments of the present invention, $R_1$ and $R_2$ are each independently $C_{4-24}$ branched alkyl or $C_{4-24}$ branched alkenyl, further preferably $C_{4-12}$ branched alkyl. Particularly, $R_1$ and $R_2$ are each independently the following fragment:

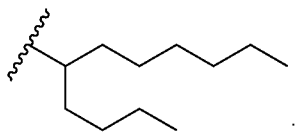 [SMILES: *C(CCCC)CCCCCC]

[Specific Compounds]

The present invention provides a series of specific compounds, as described in the above <second aspect>.

[Lipid Carrier]

The present invention provides a lipid carrier, which includes any one of the above-mentioned compounds or the pharmaceutically acceptable salt, stereoisomer, tautomer, solvate, chelate, non-covalent complex or prodrug thereof. Such lipid carrier has a high entrapment efficiency to a nucleic acid drug, which greatly improves in-vivo delivery efficiency of the nucleic acid drug.

In some specific embodiments of the present invention, the lipid carrier includes a first lipid compound and a second lipid compound, wherein, the first lipid compound includes any one of the above-mentioned compounds or the pharmaceutically acceptable salt, stereoisomer, tautomer, solvate, chelate, non-covalent complex or prodrug thereof as well as cationic lipid, and the second lipid compound includes one or a combination of two or more of anionic lipid, neutral lipid, sterol and amphiphilic lipid.

In some specific embodiments of the present invention, the cationic lipid includes one or a combination of two or more of DLinDMA, DODMA, DLin-MC2-MPZ, DLin-KC2-DMA, DOTAP, C12-200, DC-Chol and DOTMA.

In some specific embodiments of the present invention, the anionic lipid includes one or a combination of two or more of phosphatidyl serine, phosphatidyl inositol, phosphatidic acid, phosphatidyl glycerol, DOPG, DOPS and dimyristoyl phosphatidylglycerol.

In some specific embodiments of the present invention, the neutral lipid includes at least one of DOPE, DSPC, DPPC, DOPC, DPPG, POPC, POPE, DPPE, DMPE, DSPE and SOPE or its lipid modified by an anionic or cationic modifying group. The anionic or cationic modifying group is not limited.

In some specific embodiments of the present invention, the amphiphilic lipid includes one or a combination of two or more of PEG-DMG, PEG-c-DMG, PEG-C14, PEG-c-DMA, PEG-DSPE, PEG-PE, PEG-modified ceramide, PEG-modified dialkylamine, PEG-modified diacylglycerol, Tween-20, Tween-80, PEG-DPG, PEG-s-DMG, DAA, PEG-c-DOMG and GalNAc-PEG-DSG In some specific embodiments of the present invention, in the lipid carrier, a molar ratio of the first lipid compound to the anionic lipid to the neutral lipid to the sterol to the amphiphilic lipid is (20-65):(0-20):(5-25):(25-55):(0.3-15); exemplarily, the molar ratio of the first lipid compound to the anionic lipid to the neutral lipid to the sterol to the amphiphilic lipid can be 20:20:5:50:5, 30:5:25:30:10, 20:5:5:55:15, 65:0:9.7:25:0.3, etc.

Wherein, in the first lipid compound, a molar ratio of any one of above-mentioned compounds or the pharmaceutically acceptable salt, stereoisomer, tautomer, solvate, chelate, non-covalent complex or prodrug thereof to the cationic lipid is (1-10):(0-10); exemplarily, the molar ratio can be 1:1, 1:2, 1:5, 1:7.5, 1:10, 2:1, 5:1, 7.5:1, 10:1, etc.

In some preferred embodiments of the present invention, in the lipid carrier, the molar ratio of the first lipid compound to the anionic lipid to the neutral lipid to the sterol to the amphiphilic lipid is (20-55):(0-13):(5-25):(25-51.5):(0.5-15);

wherein, in the first lipid compound, the molar ratio of any one of the above-mentioned compounds or the pharmaceutically acceptable salt, stereoisomer, tautomer, solvate, chelate, non-covalent complex or prodrug thereof to the cationic lipid is (3-4):(0-5).

[Nucleic Acid Lipid Nanoparticle Composition]

The nucleic acid lipid nanoparticle composition provided by the present invention includes any one of the above-mentioned compounds or the pharmaceutically acceptable salt, stereoisomer, tautomer, solvate, chelate, non-covalent complex or prodrug thereof or the above-mentioned lipid carrier, as well as a nucleic acid drug;

In some preferred embodiments of the present invention, the nucleic acid drug includes one or a combination of two or more of DNA, siRNA, mRNA, dsRNA, antisense nucleic acid, microRNA, antisense microRNA, antagomir, a microRNA inhibitor, a microRNA activator and immunostimulatory nucleic acid.

In some preferred embodiments of the present invention, a mass ratio of the nucleic acid drug to any one of the above-mentioned compounds or the pharmaceutically acceptable salt, stereoisomer, tautomer, solvate, chelate, non-covalent complex or prodrug thereof is 1:(3-40), or, a mass ratio of the nucleic acid drug to the above-mentioned lipid carrier is 1:(3-40). Exemplarily, the above-mentioned mass ratio is 1:3, 1:5, 1:10, 1:15, 1:20, 1:30, etc.

[Pharmaceutical Preparation]

The present invention provides a pharmaceutical preparation, including any one of the above-mentioned compounds or the pharmaceutically acceptable salt, stereoisomer, tautomer, solvate, chelate, non-covalent complex or prodrug thereof, or the above-mentioned lipid carrier, or the above-mentioned nucleic acid lipid nanoparticle composition, as well as a pharmaceutically acceptable excipient, carrier and diluent agent.

In some preferred embodiments of the present invention, the pharmaceutical preparation has a particle size of 30-500 nm, exemplarily, the particle size can be 30 nm, 50 nm, 100 nm, 150 nm, 250 nm, 350 nm, 500 nm, etc.

In some preferred embodiments of the present invention, the entrapment efficiency of the nucleic acid drug in the pharmaceutical preparation is greater than 50%.

[Preparation Method]

The experimental methods in the following examples are all routine methods, unless particularly stated; and the reagents and materials all can be commercially available, unless particularly stated.

In the present invention, an "equivalent (eq)" ratio refers to a molar ratio of a solvent or drug.

In the present invention, "suitable amount" means that the amount of the added solvent or drug has a large adjustable range, and has little effect on a synthesis result, which may not be specifically limited.

In the following examples, solvents and drugs used are both analytically pure or chemically pure; the solvents are all re-distilled before use; and anhydrous solvents are all treated in accordance with a standard method or a literature method.

EXAMPLES

Example 1 Synthesis of Compound 1

2-hexyldecanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl acrylate (1.0 eq) was added, and a reaction was carried out at room temperature overnight.

After 4-hydroxybutyl acrylate was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then ethanolamine (1.0 eq) was added, stirring was performed at 35° C. overnight, after ethanolamine was monitored to be completely reacted by TLC, the resulting reaction solution was concentrated, and column chromatography was performed to obtain a compound 1. $^1$H NMR (400 MHz, CDCl$_3$) δ 4.09-4.05 (m, 8H), 3.57-3.54 (t, 2H), 2.80-2.76 (t, 4H), 2.68-2.63 (m, 2H), 2.46-2.42 (t, 4H), 2.32-2.25 (m, 2H), 1.69-1.13 (m, 56H), 0.90-0.83 (m, 12H).

Example 2 Synthesis of Compound 2

2-hexyldecanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl acrylate (1.0 eq) was added, and a reaction was carried out at room temperature overnight. After 4-hydroxybutyl acrylate was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then 3-amino-1-propanol (1.0 eq) was added, stirring was performed at 35° C. overnight, after 3-amino-1-propanol was monitored to be completely reacted by TLC, the resulting reaction solution was concentrated, and column chromatography was performed to obtain a compound 2. $^1$H NMR (400 MHz, CDCl$_3$) δ 4.10-4.06 (m, 8H), 3.71-3.68 (t, 2H), 2.79-2.75 (t, 4H), 2.62-2.59 (m, 2H), 2.49-2.45 (t, 4H), 2.33-2.24 (m, 2H), 1.72-1.13 (m, 58H), 0.90-0.83 (m, 12H).

Example 3 Synthesis of Compound 3

2-hexyldecanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl acrylate (1.0 eq) was added, and a reaction was carried out at room temperature overnight. After 4-hydroxybutyl acrylate was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then 4-amino-1-butanol (1.0 eq) was added, stirring was performed at 35° C. overnight, after 4-amino-1-butanol was monitored to be completely reacted by TLC, the resulting reaction solution was concentrated, and column chromatography was performed to obtain a compound 3. $^1$H NMR (400 MHz, CDCl$_3$) δ 4.10-4.06 (m, 8H), 3.71-3.68 (t, 2H), 2.79-2.75 (t, 4H), 2.62-2.59 (m, 2H), 2.49-2.45 (t, 4H), 2.33-2.24 (m, 2H), 1.72-1.13 (m, 60H), 0.90-0.83 (m, 12H).

Example 4 Synthesis of Compound 4

2-hexyldecanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl acrylate (1.0 eq) was added, and a reaction was carried out at room temperature overnight.

After 4-hydroxybutyl acrylate was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then 5-amino-1-pentanol (1.0 eq) was added, stirring was performed at 35° C. overnight, after 5-amino-1-pentanol was monitored to be completely reacted by TLC, the resulting reaction solution was concentrated, and column chromatography was performed to obtain a compound 4. $^1$H NMR (400 MHz, CDCl$_3$) δ 4.10-4.06 (m, 8H), 3.71-3.68 (t, 2H), 2.79-2.75 (t, 4H), 2.62-2.59 (m, 2H), 2.49-2.45 (t, 4H), 2.33-2.24 (m, 2H), 1.72-1.13 (m, 62H), 0.90-0.83 (m, 12H).

Example 5 Synthesis of Compound 5

2-butyloctanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl acrylate (1.0 eq) was added, and a reaction was carried out at room temperature overnight. After 4-hydroxybutyl acrylate was confirmed to be completely reacted by TLC, 1 M hydrochloric acid was added to adjust pH to be 6-7, extraction was for multiple times, and column chromatography was performed to obtain a colorless transparent liquid.

The above obtained colorless transparent liquid (2.3 eq) was dissolved in a suitable amount of methanol, then ethanolamine (1.0 eq) was added, stirring was performed at 35° C. overnight, after ethanolamine was monitored to be completely reacted by TLC, the resulting reaction solution was concentrated, and column chromatography was performed to obtain a compound 5. $^1$H NMR (400 MHz, CDCl$_3$) δ 4.09-4.05 (m, 8H), 3.57-3.54 (t, 2H), 2.80-2.76 (t, 4H), 2.68-2.56 (m, 2H), 2.46-2.42 (t, 4H), 2.33-2.25 (m, 2H), 1.72-1.14 (m, 40H), 0.86-0.83 (m, 12H).

Example 6 Synthesis of Compound 6

2-butyloctanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl acrylate (1.0 eq) was added, and a reaction was carried out at room temperature overnight. After 4-hydroxybutyl acrylate was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then 3-amino-1-propanol (1.0 eq) was added, stirring was performed at 35° C. overnight, after 3-amino-1-propanol was monitored to be completely reacted by TLC, the resulting reaction solution was concentrated, and column chromatography was performed to obtain a compound 6. $^1$H NMR (400 MHz, CDCl$_3$) δ 4.09-4.05 (m, 8H), 3.57-3.54 (t, 2H), 2.80-2.76 (t, 4H), 2.68-2.56 (m, 2H), 2.46-2.42 (t, 4H), 2.33-2.25 (m, 2H), 1.72-1.14 (m, 42H), 0.86-0.83 (m, 12H).

Example 7 Synthesis of Compound 7

2-butyloctanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl acrylate (1.0 eq) was added, and a reaction was carried out at room temperature overnight. After 4-hydroxybutyl acrylate was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then 4-amino-1-butanol (1.0 eq) was added, stirring was performed at 35° C. overnight, after 4-amino-1-butanol was monitored to be completely reacted by TLC, the resulting reaction solution was concentrated, and column chromatography was performed to obtain a compound 7. $^1$H NMR (400 MHz, DMSO-d$_6$) δ 4.05-3.90 (m, 8H), 3.42-3.34 (m, 2H), 3.30-3.28 (m, 2H), 2.66-2.63 (t, 4H), 2.37-2.34 (m, 4H), 2.29-2.23 (m, 2H), 1.72-1.14 (m, 44H), 0.86-0.83 (m, 12H).

Example 8 Synthesis of Compound 8

2-butyloctanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl acrylate (1.0 eq) was added, and a reaction was carried out at room temperature overnight. After 4-hydroxybutyl acrylate was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then 5-amino-1-pentanol (1.0 eq) was added, stirring was performed at 35° C. overnight, after 5-amino-1-pentanol was monitored to be completely reacted by TLC, the resulting reaction solution was concentrated, and column chromatography was performed to obtain a compound 8. $^1$H NMR (400 MHz, CDCl$_3$) δ 4.09-4.05 (m, 8H), 3.57-3.54 (t, 2H), 2.80-2.76 (t, 4H), 2.68-2.56 (m, 2H), 2.46-2.42 (t, 4H), 2.33-2.25 (m, 2H), 1.72-1.14 (m, 46H), 0.86-0.83 (m, 12H).

Example 9 Synthesis of Compound 9

2-hexyldecanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl vinyl ether (1.0 eq) was added, and a reaction was carried out at room temperature overnight. After 4-hydroxybutyl vinyl ether was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then 4-amino-1-butanol (1.0 eq) was added, stirring was performed at 35° C. overnight, after 4-amino-1-butanol was monitored to be completely reacted by TLC, the resulting reaction solution was concentrated, and column chromatography was performed to obtain a compound 9. $^1$H NMR (400 MHz, CDCl$_3$) δ 4.08-4.05 (m, 4H), 3.56-3.35 (m, 10H), 2.83-2.80 (t, 2H), 2.61-2.53 (m, 4H), 2.35-2.25 (m, 2H), 1.73-1.14 (m, 60H), 0.86-0.83 (m, 12H).

Example 10 Synthesis of Compound 10

2-hexyldecanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl vinyl ether (1.0 eq) was added, and a reaction was carried out at room temperature overnight. After 4-hydroxybutyl vinyl ether was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then 5-amino-1-pentanol (1.0 eq) was added, stirring was performed at 35° C. overnight, after 5-amino-1-pentanol was monitored to be completely reacted by TLC, the resulting reaction solution was concentrated, and column chromatography was performed to obtain a compound 10. $^1$H NMR (400 MHz, CDCl$_3$) δ 4.08-4.04 (m, 4H), 3.56-3.34 (m, 10H), 2.83-2.78 (t, 2H), 2.61-2.53 (m, 4H), 2.35-2.25 (m, 2H), 1.74-1.12 (m, 62H), 0.86-0.83 (m, 12H).

Example 11 Synthesis of Compound 11

2-butyloctanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl vinyl ether (1.0 eq) was added, and a reaction was carried out at room temperature overnight.

After 4-hydroxybutyl vinyl ether was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then 4-amino-1-butanol (1.0 eq) was added, stirring was performed at 35° C. overnight, after 4-amino-1-butanol was monitored to be completely reacted by TLC, the resulting reaction solution was concentrated, and column chromatography was performed to obtain a compound 11. $^1$H NMR (400 MHz, DMSO-d$_6$) δ 4.05-3.90 (m, 8H), 3.42-3.34 (m, 2H), 3.30-3.28 (m, 2H), 2.66-2.63 (t, 4H), 2.37-2.34 (m, 4H), 2.29-2.23 (m, 2H), 1.72-1.14 (m, 44H), 0.86-0.83 (m, 12H).

Example 12 Synthesis of Compound 12

2-butyloctanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl vinyl ether (1.0 eq) was added, and a reaction was carried out at room temperature overnight. After 4-hydroxybutyl vinyl ether was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then 5-amino-1-pentanol (1.0 eq) was added, stirring was performed at 35° C. overnight, after 5-amino-1-pentanol was monitored to be completely reacted by TLC, the resulting reaction solution was concentrated, and column chromatography was performed to obtain a compound 12. $^1$H NMR (400 MHz, CDCl$_3$) δ 4.09-4.05 (m, 8H), 3.57-3.54 (t, 2H), 2.80-2.76 (t, 4H), 2.68-2.56 (m, 2H), 2.46-2.42 (t, 4H), 2.33-2.25 (m, 2H), 1.72-1.14 (m, 46H), 0.86-0.83 (m, 12H).

Example 13 Synthesis of Compound 13

2-butyloctanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl acrylate (1.0 eq) was added, and a reaction was carried out at room temperature overnight.

After 4-hydroxybutyl acrylate was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then 1-(3-aminopropyl)imidazole (1.0 eq) was added, stirring was performed at 35° C. overnight, after 1-(3-aminopropyl) imidazole was monitored to be completely reacted by TLC, the resulting reaction solution was concentrated, and column chromatography was performed to obtain a compound 13. $^1$H NMR (400 MHz, CDCl$_3$) δ 7.49 (s, 1H), 7.03 (s, 1H), 6.93 (s, 1H), 4.15-4.03 (t, 8H), 3.96-3.93 (t, 2H), 2.75-2.71 (t, 4H), 2.41-2.26 (m, 8H), 1.93-1.86 (m, 2H), 1.71-1.14 (m, 40H), 0.87-0.84 (m, 12H).

Example 14 Synthesis of Compound 14

2-hexyldecanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl acrylate (1.0 eq) was added, and a reaction was carried out at room temperature overnight. After 4-hydroxybutyl acrylate was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then 1-(3-aminopropyl)imidazole (1.0 eq) was added, stirring was performed at 35° C. overnight, after 1-(3-aminopropyl) imidazole was monitored to be completely reacted by TLC, the resulting reaction solution was concentrated, and column chromatography was performed to obtain a compound 14. $^1$H NMR (400 MHz, CDCl$_3$) δ 7.49 (s, 1H), 7.03 (s, 1H), 6.93 (s, 1H), 4.15-4.03 (t, 8H), 3.96-3.93 (t, 2H), 2.75-2.71 (t, 4H), 2.41-2.26 (m, 8H), 1.93-1.86 (m, 2H), 1.71-1.14 (m, 56H), 0.87-0.84 (m, 12H).

Example 15 Synthesis of Compound 24

2-butyloctanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl acrylate (1.0 eq) was added, and a reaction was carried out at room temperature overnight. After 4-hydroxybutyl acrylate was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then diglycolamine (1.0 eq) was added, stirring was performed at 35° C. overnight, after diglycolamine was monitored to be completely reacted by TLC, the resulting reaction solution was concentrated, and column chromatography was performed to obtain a compound 24. $^1$H NMR (400 MHz, CDCl$_3$) δ 4.06-4.03 (m, 8H), 3.56-3.54 (t, 2H), 3.52-3.49 (m, 4H), 2.80-2.76 (t, 4H), 2.67-2.62 (m, 2H), 2.46-2.42 (t, 4H), 2.32-2.25 (m, 2H), 1.71-1.12 (m, 40H), 0.91-0.84 (m, 12H).

Example 16 Synthesis of Compound 25

2-hexyldecanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl acrylate (1.0 eq) was added, and a reaction was carried out at room temperature overnight. After 4-hydroxybutyl acrylate was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then diglycolamine (1.0 eq) was added, stirring was performed at 35° C. overnight, after diglycolamine was monitored to be completely reacted by TLC, the resulting reaction solution was concentrated, and column chromatography was performed to obtain a compound 25. $^1$H NMR (400 MHz, CDCl$_3$) δ 4.07-4.03 (m, 8H), 3.57-3.54 (t, 2H), 3.50-3.48

(m, 4H), 2.80-2.76 (t, 4H), 2.67-2.62 (m, 2H), 2.46-2.42 (t, 4H), 2.32-2.25 (m, 2H), 1.73-1.12 (m, 56H), 0.91-0.84 (m, 12H).

Example 17 Synthesis of Compound 29

2-butyloctanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl acrylate (1.0 eq) was added, and a reaction was carried out at room temperature overnight. After 4-hydroxybutyl acrylate was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then 3-ethoxypropylamine (1.0 eq) was added, stirring was performed at 35° C. overnight, after 3-ethoxypropylamine was monitored to be completely reacted by TLC, the resulting reaction solution was concentrated, and column chromatography was performed to obtain a compound 29. $^1$H NMR (400 MHz, CDCl$_3$) δ 4.07-4.02 (m, 8H), 3.46-3.35 (m, 4H), 2.79-2.75 (t, 4H), 2.61-2.59 (m, 2H), 2.48-2.46 (t, 4H), 2.32-2.24 (m, 2H), 1.72-1.13 (m, 42H), 1.00-0.97 (m, 3H), 0.90-0.83 (m, 12H).

Example 18 Synthesis of Compound 30

2-butyloctanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl acrylate (1.0 eq) was added, and a reaction was carried out at room temperature overnight. After 4-hydroxybutyl acrylate was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then methyl 4-aminobutyrate (1.0 eq) was added, stirring was performed at 35° C. overnight, after methyl 4-aminobutyrate was monitored to be completely reacted by TLC, the resulting reaction solution was concentrated, and column chromatography was performed to obtain a compound 30. $^1$H NMR (400 MHz, CDCl$_3$) δ 4.09-4.03 (m, 8H), 3.71 (s, 3H), 2.86-2.81 (t, 4H), 2.51-2.46 (m, 8H), 2.32-2.24 (m, 2H), 1.92-1.87 (m, 2H), 1.72-1.13 (m, 40H), 0.90-0.83 (m, 12H).

Example 19 Synthesis of Compound 31

2-hexyldecanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl vinyl ether (1.0 eq) was added, and a reaction was carried out at room temperature overnight. After 4-hydroxybutyl vinyl ether was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then diglycolamine (1.0 eq) was added, stirring was performed at 35° C. overnight, after diglycolamine was monitored to be completely reacted by TLC, the resulting reaction solution was concentrated, and column chromatography was performed to obtain a compound 31. $^1$H NMR (400 MHz, CDCl$_3$) δ 4.08-4.04 (m, 4H), 3.56-3.34 (m, 10H), 3.42-3.38 (m, 4H), 2.61-2.53 (m, 6H), 2.35-2.25 (m, 2H), 1.74-1.12 (m, 56H), 0.86-0.83 (m, 12H).

Example 20 Synthesis of Compound 35

2-butyloctanoic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-hydroxybutyl vinyl ether (1.0 eq) was added, and a reaction was carried out at room temperature overnight. After 4-hydroxybutyl vinyl ether was confirmed to be completely reacted by TLC, 1 M hydrochloric acid was added to adjust pH to be 6-7, extraction was performed for multiple times, and column chromatography was performed to obtain a colorless transparent liquid.

The above obtained colorless transparent liquid (2.3 eq) was dissolved in a suitable amount of methanol, then diglycolamine (1.0 eq) was added, stirring was performed at 35° C. overnight, after diglycolamine was monitored to be completely reacted by TLC, the resulting reaction solution was concentrated, and column chromatography was performed to obtain a compound 35. $^1$H NMR (400 MHz, CDCl$_3$) δ 4.07-4.04 (m, 4H), 3.55-3.34 (m, 10H), 3.41-3.38 (m, 4H), 2.61-2.53 (m, 6H), 2.35-2.25 (m, 2H), 1.74-1.12 (m, 40H), 0.86-0.83 (m, 12H).

Example 21 Synthesis of Compound 36

6-bromocaproic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 4-heptyloxy-1-butanol (1.0 eq) was added, and a reaction was carried out at room temperature overnight. After confirmation by TLC, 1 M hydrochloric acid was added to adjust pH to be 6-7, extraction was performed for multiple times, and column chromatography was performed to obtain an intermediate 1.

8-bromocaprylic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 9-heptadecanol (1.0 eq) was added, and a reaction was carried out at room temperature overnight. After confirmation by TLC, 1 M hydrochloric acid was added to adjust pH to be 6-7, extraction was performed for multiple times, and column chromatography was performed to obtain an intermediate 2.

Ethanolamine (10.0 eq) was dissolved in a suitable amount of anhydrous DMF, stirring was performed, potassium carbonate (2.0 eq) was added under a nitrogen atmosphere. After the addition was finished, the intermediate 1 (1.0 eq) was dissolved in a suitable amount of anhydrous DMF, and the resulting solution was added dropwise under a nitrogen atmosphere by using a constant pressure dropping funnel. After the addition was finished, the mixture was heated to 80° C., and a reaction was carried out for 16 h while stirring under a nitrogen atmosphere. After confirmation by TLC, extraction was performed for multiple times, and column chromatography was performed to obtain an intermediate 3.

The intermediate 3 (1.0 eq) was dissolved in a suitable amount of anhydrous DMF, stirring was performed, and potassium carbonate (2.0 eq) was added under a nitrogen atmosphere. After the addition was finished, the intermediate 2 (1.2 eq) was dissolved in a suitable amount of anhydrous DMF, and the resulting solution was added dropwise under a nitrogen atmosphere by using a constant pressure dropping funnel. After the addition was finished, the mixture was heated to 80° C., and a reaction was carried out for 16 h while stirring under a nitrogen atmosphere. After confirmation by TLC, extraction was performed for multiple times, and column chromatography was performed to obtain a compound 36. $^1$H NMR (400 MHz, CDCl$_3$) δ 4.88-4.82 (m, 1H), 4.07-4.03 (m, 2H), 3.96-3.93 (m, 2H), 3.74-3.76 (m, 4H), 3.11-3.09 (m, 2H), 3.02-2.98 (m, 4H), 2.31-2.26 (m, 4H), 1.87-1.17 (m, 58H), 0.89-0.86 (m, 9H).

Example 22 Synthesis of Compound 37

Nonanoic acid (1.0 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, ethylene glycol (1.5 eq) was added, and a reaction was carried out at room temperature overnight. After confirmation by TLC, 1 M hydrochloric acid was added to adjust pH to be 6-7, extraction was performed for multiple times, and column chromatography was performed to obtain an intermediate 1.

6-bromocaproic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, the intermediate 1 (1.0 eq) was added, and a reaction was carried out at room temperature overnight. After confirmation by TLC, 1 M hydrochloric acid was added to adjust pH to be 6-7, extraction was performed for multiple times, and column chromatography was performed to obtain an intermediate 2.

8-bromocaprylic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 9-heptadecanol (1.0 eq) was added, and a reaction was carried out at room temperature overnight. After confirmation by TLC, 1 M hydrochloric acid was added to adjust pH to be 6-7, extraction was performed for multiple times, and column chromatography was performed to obtain an intermediate 3.

Ethanolamine (10.0 eq) was dissolved in a suitable amount of anhydrous DMF, stirring was performed, and potassium carbonate (2.0 eq) was added under a nitrogen atmosphere. After the addition was finished, the intermediate 2 (1.0 eq) was dissolved in a suitable amount of anhydrous DMF, and the resulting solution was added dropwise under a nitrogen atmosphere by using a constant pressure dropping funnel. After the addition was finished, the mixture was heated to 80° C., and a reaction was carried out for 16 h while stirring under a nitrogen atmosphere. After confirmation by TLC, extraction was performed for multiple times, and column chromatography was performed to obtain an intermediate 4.

The intermediate 4 (1.0 eq) was dissolved in a suitable amount of anhydrous DMF, stirring was performed, and potassium carbonate (2.0 eq) was added under a nitrogen atmosphere. After the addition was finished, the intermediate 3 (1.2 eq) was dissolved in a suitable amount of anhydrous DMF, and the resulting solution was added dropwise under a nitrogen atmosphere by using a constant pressure dropping funnel. After the addition was finished, the mixture was heated to 80° C., and a reaction was carried out for 16 h while stirring under a nitrogen atmosphere. After confirmation by TLC, extraction was performed for multiple times, and column chromatography was performed to obtain a compound 37. $^1$H NMR (400 MHz, CDCl$_3$) δ 4.88-4.82 (m, 1H), 4.34-4.30 (m, 4H), 3.95-3.93 (m, 2H), 3.12-3.08 (m, 2H), 3.02-2.98 (m, 4H), 2.31-2.22 (m, 6H), 1.91-1.16 (m, 56H), 0.89-0.86 (m, 9H).

Example 23 Synthesis of Compound 38

Succinic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, undecanol (1.0 eq) was added, and a reaction was carried out at room temperature overnight. After confirmation by TLC, 1 M hydrochloric acid was added to adjust pH to be 6-7, extraction was performed for multiple times, and column chromatography was performed to obtain an intermediate 1.

The intermediate 1 (1.0 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 2-bromoethanol (1.5 eq) was added, and a reaction was carried out at room temperature overnight. After confirmation by TLC, 1 M hydrochloric acid was added to adjust pH to be 6-7, extraction was performed for multiple times, and column chromatography was performed to obtain an intermediate 2.

8-bromocaprylic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 9-heptadecanol (1.0 eq) was added, and a reaction was carried out at room temperature overnight. After confirmation by TLC, 1 M hydrochloric acid was added to adjust pH to be 6-7, extraction was performed for multiple times, and column chromatography was performed to obtain an intermediate 3.

Ethanolamine (10.0 eq) was dissolved in a suitable amount of anhydrous DMF, stirring was performed, and potassium carbonate (2.0 eq) was added under a nitrogen atmosphere. After the addition was finished, the intermediate 2 (1.0 eq) was dissolved in a suitable amount of anhydrous DMF, and the resulting solution was added dropwise under a nitrogen atmosphere by using a constant pressure dropping funnel. After the addition was finished, the mixture was heated to 80° C., and a reaction was carried out for 16 h while stirring under a nitrogen atmosphere. After confirmation by TLC, extraction was performed for multiple times, and column chromatography was performed to obtain an intermediate 4.

The intermediate 4 (1.0 eq) was dissolved in a suitable amount of anhydrous DMF, stirring was performed, and potassium carbonate (2.0 eq) was added under a nitrogen atmosphere. After the addition was finished, the intermediate 3 (1.2 eq) was dissolved in a suitable amount of anhydrous DMF, and the resulting solution was added dropwise under a nitrogen atmosphere by using a constant pressure dropping funnel. After the addition was finished, the mixture was heated to 80° C., and a reaction was carried out for 16 h while stirring under a nitrogen atmosphere. After confirmation by TLC, extraction was performed for multiple times, and column chromatography was performed to obtain a compound 38. $^1$H NMR (400 MHz, CDCl$_3$) δ 4.90-4.84 (m, 1H), 4.35-4.29 (m, 4H), 3.96-3.93 (m, 2H), 3.12-3.08 (m, 2H), 3.04-2.98 (m, 4H), 2.76-2.74 (m, 4H), 2.35-2.29 (m, 2H), 1.84-1.17 (m, 56H), 0.89-0.86 (m, 9H).

Example 24 Synthesis of Compound 39

6-bromocaproic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, undecanol (1.0 eq) was added, and a reaction was carried out at room temperature overnight. After confirmation by TLC, 1 M hydrochloric acid was added to adjust pH to be 6-7, extraction was performed for multiple times, and column chromatography was performed to obtain an intermediate 1.

Adipic acid (1.5 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 9-heptadecanol (1.0 eq) was added, and a reaction was carried out at room temperature overnight. After confirmation by TLC, 1 M hydrochloric acid was added to adjust pH to be 6-7, extraction was performed for multiple times, and column chromatography was performed to obtain an intermediate 2.

The intermediate 2 (1.50 eq) was dissolved in a suitable amount of dichloromethane, stirring was performed, EDC (1.5 eq), DMAP (0.5 eq) and triethylamine (1.0 eq) were added, the mixture was stirred at room temperature for 0.5 h, 2-bromoethanol (1.5 eq) was added, and a reaction was carried out at room temperature overnight. After confirmation by TLC, 1 M hydrochloric acid was added to adjust pH to be 6-7, extraction was performed for multiple times, and column chromatography was performed to obtain an intermediate 3.

Ethanolamine (10.0 eq) was dissolved in a suitable amount of anhydrous DMF, stirring was performed, and potassium carbonate (2.0 eq) was added under a nitrogen atmosphere. After the addition was finished, the intermediate 3 (1.0 eq) was dissolved in a suitable amount of anhydrous DMF, and the resulting solution was added dropwise under a nitrogen atmosphere by using a constant pressure dropping funnel. After the addition was finished, the mixture was heated to 80° C., and a reaction was carried out for 16 h while stirring under a nitrogen atmosphere. After confirmation by TLC, extraction was performed for multiple times, and column chromatography was performed to obtain an intermediate 4.

The intermediate 4 (1.0 eq) was dissolved in a suitable amount of anhydrous DMF, stirring was performed, and potassium carbonate (2.0 eq) was added under a nitrogen atmosphere. After the addition was finished, the intermediate 1 (1.2 eq) was dissolved in a suitable amount of anhydrous DMF, and the resulting solution was added dropwise under a nitrogen atmosphere by using a constant pressure dropping funnel. After the addition was finished, the mixture was heated to 80° C., and a reaction was carried out for 16 h while stirring under a nitrogen atmosphere. After confirmation by TLC, extraction was performed for multiple times, and column chromatography was performed to obtain a compound 39. $^1$H NMR (400 MHz, CDCl$_3$) δ 4.89-4.82 (m, 1H), 4.35-4.13 (m, 4H), 3.97-3.93 (m, 2H), 3.11-3.09 (m, 2H), 3.02-2.98 (m, 4H), 2.35-2.23 (m, 6H), 1.86-1.16 (m, 56H), 0.88-0.86 (m, 9H).

Example 25

Compounds 1-8 were respectively dissolved in ethanol together with cholesterol, DSPC, PEG-DMG at a molar ratio of 50:38.5:10:1.5, luciferase mRNA was dissolved in a 50 mM citric acid buffered saline solution with a pH of 4.0, a volume ratio of the two solutions was 1:3, two phases were rapidly mixed by using microfluidics and a buffer environment was replaced into PBS with a pH of 7.4 by using dialysis or a tangential flow, so as to remove ethanol, and eight LNP@mRNAs were respectively prepared.

The particle size, PDI and entrapment efficiency of each LNP@mRNA were tested, and the results were as shown in Table 1. The results show that the particle size of the LNP@mRNA jointly prepared from compounds 1, 2, 3, and 4 and other three lipids are small; except a compound 6, the entrapment efficiencies to mRNA by the LNP@mRNA jointly prepared from other seven compounds and other three lipids are all greater than 80%. Thus, it can be seen that the entrapment efficiency to the nucleic acid drug by the compound provided by the present invention is high, and, using this compound as a carrier can improve the in-vivo delivery efficiency of the nucleic acid drug.

TABLE 1

Particle size, PDI, Zeta, and entrapment efficiency of each LNP@mRNA

| Compound | Particle size (nm) | PDI | Zeta (mV) | Entrapment efficiency (%) |
|---|---|---|---|---|
| 1 | 95 | 0.06 | −9 | 87 |
| 2 | 68 | 0.07 | −14 | 86 |
| 3 | 76 | 0.07 | −15 | 86 |
| 4 | 77 | 0.09 | −12 | 82 |
| 5 | 114 | 0.10 | −13 | 80 |
| 6 | 125 | 0.06 | −12 | 72 |
| 7 | 116 | 0.05 | −18 | 82 |
| 8 | 124 | 0.07 | −12 | 82 |

Figure 2:
FIG. 2 is a mouse imaging drawing of intramuscular injection of LNP@mRNA jointly prepared from a compound 7 in Example 25 and other three lipids.
Figure 3:
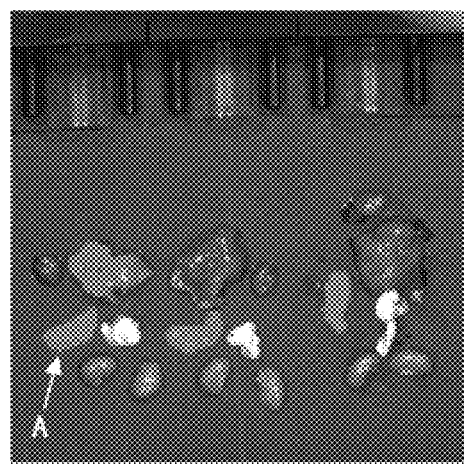
FIG. 3 is a mouse imaging anatomical drawing of intramuscular injection of LNP@mRNA jointly prepared from the compound 7 in Example 25 and other three lipids.

LNP@mRNAs prepared were respectively injected into a mouse body via a caudal vein or muscle, and after 6 hours, the fluorescence intensity and organ distribution in mice were tested. FIG. 1 is a comparison diagram of maximum fluorescence of intramuscular injection of LNP@mRNA jointly prepared from compounds 1-8 and other three lipids, and the results show that the effect of the LNP@mRNA jointly prepared from a compound 7 and other three lipids is better. FIG. 2 is a mouse imaging drawing of intramuscular injection of LNP@mRNA jointly prepared from the compound 7 and other three lipids, FIG. 3 is an imaging anatomical drawing, and the result shows that mRNA is manly expressed in spleen (as shown by A in FIG. 3). Therefore, a lipid compound with a specific structure can be chosen as a lipid carrier based on an organ in which the nucleic acid drug needs to be enriched.

Example 26

Compounds 13, and 14 and cholesterol, DOPC, and PEG-DMG were dissolved in ethanol at a molar ratio of 50:38.5:10:1.5, luciferase mRNA was dissolved in a 50 mM citric acid buffered saline solution with a pH of 4.0, a volume ratio of the two solutions was 1:3, two phases were mixed rapidly by using microfluidics and a buffer environment was replaced into PBS with a pH of 7.4 by using dialysis or a tangential flow, so as to remove ethanol, and two LNP@mRNAs were respectively prepared. The particle size, PDI and entrapment efficiency of each LNP@mRNA were tested, and the results are as shown in Table 2.

TABLE 2

Particle size, PDI, Zeta, entrapment efficiency of each LNP@mRNA

| Compound | Particle size (nm) | PDI | Zeta (mV) | Entrapment efficiency (%) |
|---|---|---|---|---|
| 13 | 156 | 0.03 | −19 | 85 |
| 14 | 122 | 0.07 | −11 | 87 |

Figure 4:
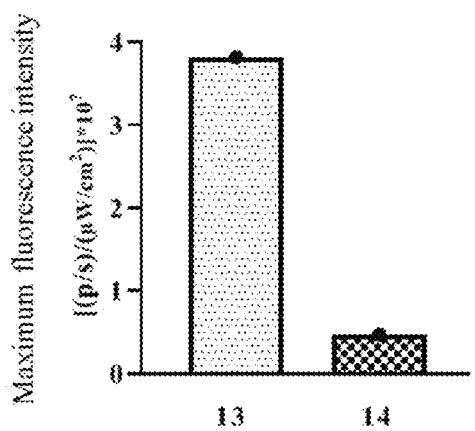
FIG. 4 is a comparison diagram of maximum fluorescence of intramuscular injection of LNP@mRNAs jointly prepared from compounds 13, and 14 in Example 26 and other three lipids.
Figure 5:
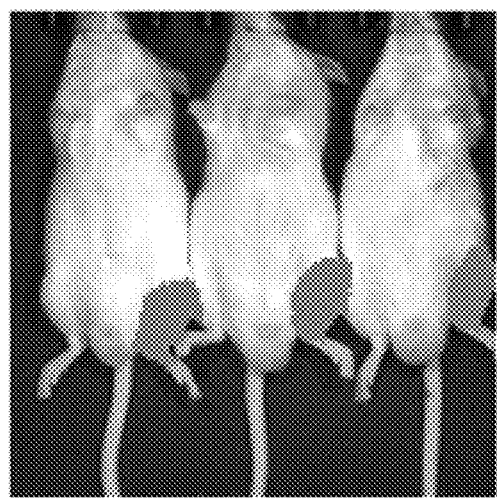
FIG. 5 is a mouse imaging drawing of intramuscular injection of LNP@mRNA jointly prepared from a compound 14 in Example 26 and other three lipids.
Figure 6:
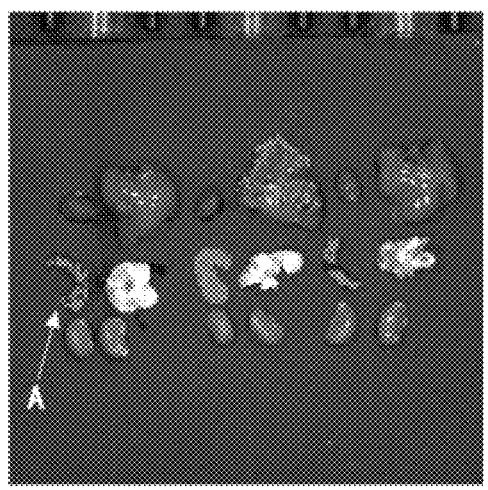
FIG. 6 is a mouse anatomical drawing of intramuscular injection of LNP@mRNA jointly prepared from the compound 14 in Example 26 and other three lipids.

LNP@mRNAs prepared were respectively injected into a mouse body via a caudal vein or muscle, and after 6 hours, the fluorescence intensity and organ distribution in mice were tested. FIG. 4 is a comparison figure of maximum fluorescence of intramuscular injection of LNP@mRNAs jointly prepared from compounds 13, and 14 and other three lipids, and the results show that the effect of LNP@mRNA jointly prepared from a compound 13 and other three lipids is better. FIG. 5 is a mouse imaging drawing of intramuscular injection of LNP@mRNA jointly prepared from a compound 14 and other three lipids, FIG. 6 is an imaging anatomical drawing, and the results show that mRNA is mainly expressed in spleen (as shown by A in FIG. 6).

Figure 7:
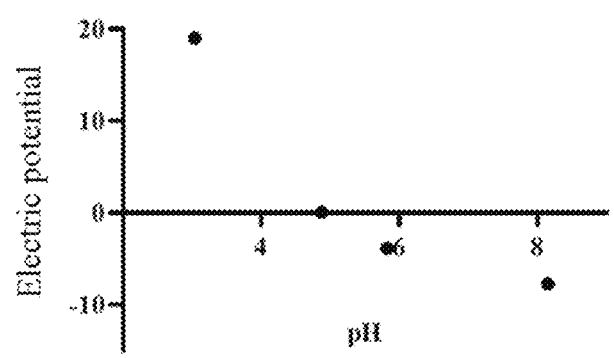
FIG. 7 shows electric potential results of LNP@mRNA jointly prepared from a compound 13 in Example 26 and other three lipids under different pHs.

FIG. 7 shows Zeta electric potentials of the LNP@mRNA jointly prepared from the compound 13 and other three lipids under different pHs, and the results show that when a pH was about 2, the LNP@mRNA presents a strong positive electricity; when the pH is close to 5, the LNP@mRNA represents electric neutrality; when the pH was greater than 8, the LNP@mRNA represents a strong electronegativity. This shows that a lipid carrier prepared by using the compound provided by the present invention and other lipid compounds can exhibit pH response.

Example 27

A compound 36 and DOTAP, cholesterol, DSPC, and PEG-DMG were dissolved in ethanol at a molar ratio of 30:20:38.5:10:1.5, luciferase mRNA was dissolved in a 50 mM citric acid buffered saline solution with a pH of 4.0, a volume ratio of the two solutions was 1:3, two phases were mixed rapidly by using microfluidics, and a buffer environment was replaced into PBS with a pH of 7.4 by using dialysis or a tangential flow to obtain LNP@mRNA. A cryoprotectant sucrose was added to obtain a nucleic acid lipid nanoparticle pharmaceutical preparation.

Example 28

A compound 38 and DOTAP, DOPS, cholesterol, DSPC, and PEG-DMG (15 mg in total) were dissolved in ethanol at a molar ratio of 20:25:15:25:5:10, luciferase mRNA (5 mg) was dissolved in a 50 mM citric acid buffered saline solution with a pH of 4.0, a volume ratio of the two solutions was 1:3, two phases were mixed rapidly by using microfluidics, and a buffer environment was replaced into PBS with a pH of 4.0 by using dialysis or a tangential flow to obtain LNP@mRNA. A cryoprotectant sucrose was added to obtain a nucleic acid lipid nanoparticle pharmaceutical preparation.

Example 29

A compound 39 and DLin-KC2-DMA, DOPG, cholesterol, DSPC, and Tween-80 (30 mg in total) were dissolved in ethanol at a molar ratio of 15:5:3:51.5:25:0.5, luciferase mRNA (1 mg) was dissolved in a 50 mM citric acid buffered saline solution with a pH of 4.0, a volume ratio of the two solutions was 1:3, two phases were mixed rapidly by using microfluidics, and a buffer environment was replaced into PBS with a pH of 7.4 by using dialysis or a tangential flow to obtain a LNP@mRNA. A cryoprotectant sucrose was added to obtain a nucleic acid lipid nanoparticle pharmaceutical preparation.

It should be noted that although the technical solution of the present invention has been introduced by means of specific examples, those skilled in the art can understand that the present invention should not be limited to the specific examples. Examples of the present invention have been described above, the above illustration is exemplary but is not exhaustive, and also not limited to the examples disclosed. Many modifications and variations are evident to those of ordinary skill in the art without departing from the scope and sprit of the examples illustrated. The selection of the terms used herein is intended to best explain the principles of the examples, practical application or technological improvement in the market, or to enable those of ordinary skill in the art to understand the examples disclosed herein.

The invention claimed is:

1. A compound of a formula (I-2), or a pharmaceutically acceptable salt, stereoisomer, or chelate thereof,

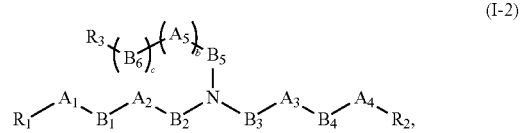

(I-2)

wherein $A_1, A_2, A_3, A_4$ and $A_5$ are each independently one or more of —O(C=O)—, —(C=O)O—, —O—, —S—S—, —NR$^a$C(=O), or —C(=O)NR$^a$—;

$B_1, B_2, B_3$ and $B_4$ are each independently $C_{1-8}$ alkylene;

$B_5$ and $B_6$ are each independently $C_{1-8}$ alkylene;

$R_1$ and $R_2$ are each independently $C_{4-8}$ branched alkyl;

$R_3$ is hydrogen, hydroxyl, hydroxyl-substituted alkyl or 5- to 7-membered heterocyclyl; wherein the 5- to 7-membered heterocyclic group is optionally substituted by $C_{1-4}$ alkyl, and contains 1 to 4 ring-forming heteroatoms, and the heteroatoms are each independently N, O or S;

$R^a$ is hydrogen or $C_{1-8}$ alkyl; and b and c are each independently 0 or 1.

2. The compound or the pharmaceutically acceptable salt, stereoisomer, or chelate thereof according to claim 1, wherein $R_3$ is hydroxyl or hydroxyl-substituted alkyl.

3. The compound or the pharmaceutically acceptable salt, stereoisomer, or chelate thereof according to claim 2, wherein the compound is selected from any one of the following compounds:

(I-2-1)
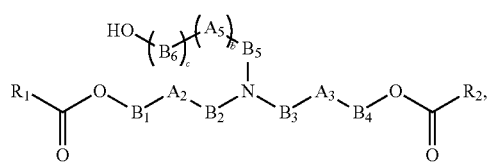

(I-2-1-1)
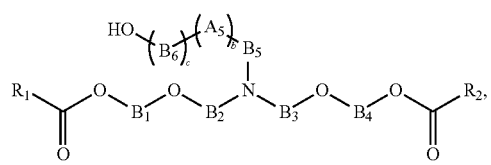

(I-2-1-2)
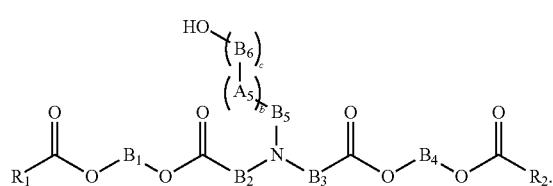

4. The compound or the pharmaceutically acceptable salt, stereoisomer, or chelate thereof according to claim 2, wherein the compound has a structure shown in formula (I-2-2):

(I-2-2)
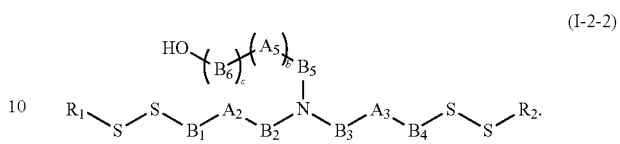

5. The compound or the pharmaceutically acceptable salt, stereoisomer, or chelate thereof according to claim 1, wherein
the compound has a structure shown in a formula (I-2-3):

(I-2-3)
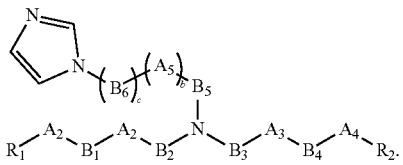
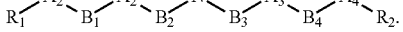

6. The compound or the pharmaceutically acceptable salt, stereoisomer, or chelate thereof according to claim 1, wherein $R_3$ is hydrogen and c is 1.

7. A compound selected from the group consisting of any one of the following compound, or a pharmaceutically acceptable salt, stereoisomer, or chelate thereof:

1
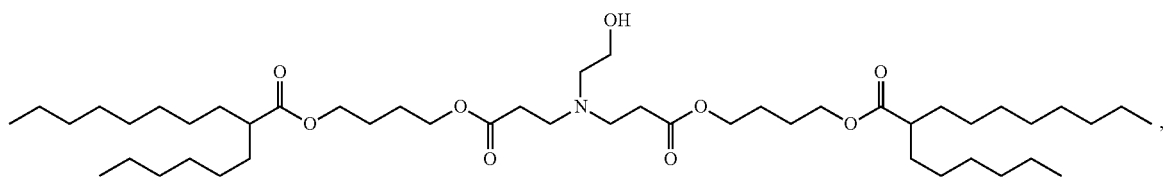

2
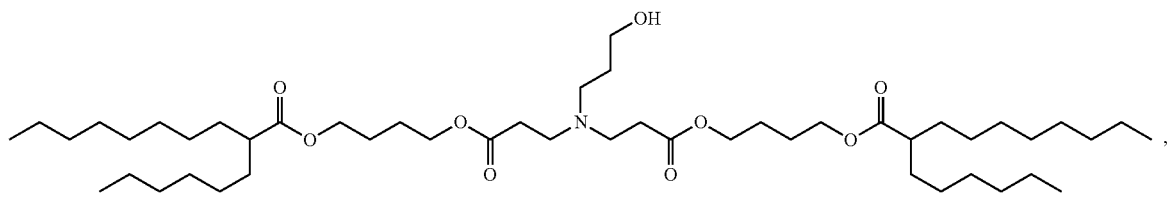

3
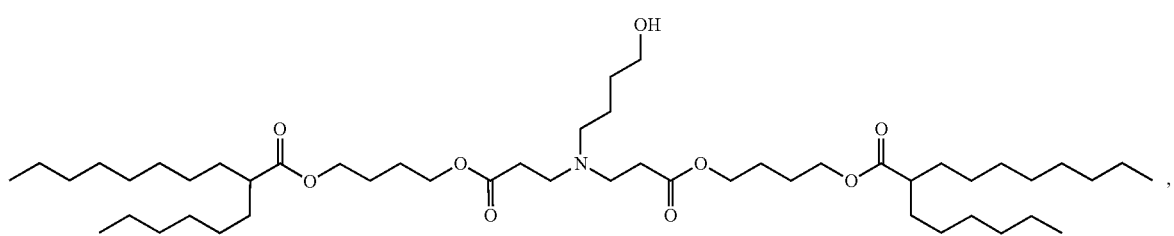

4
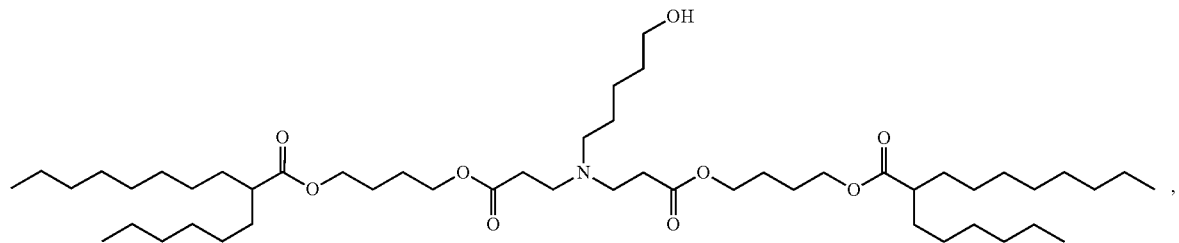
,
5
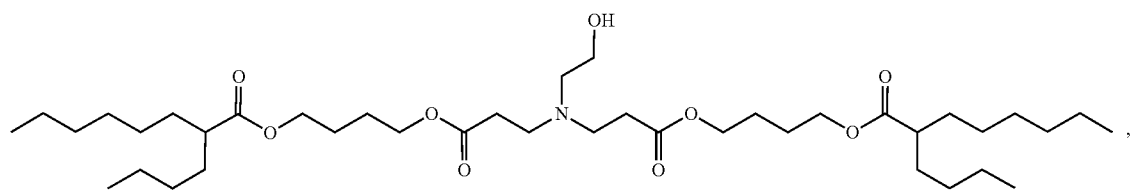
,
6
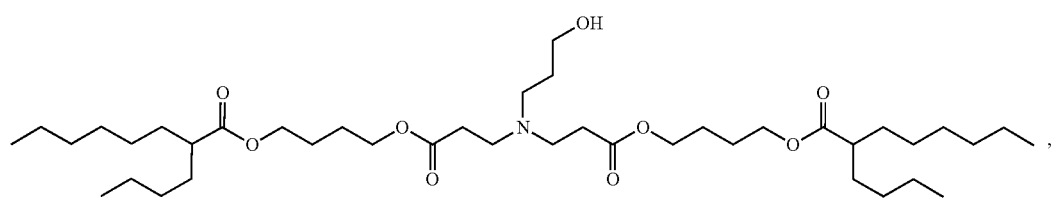
,
7
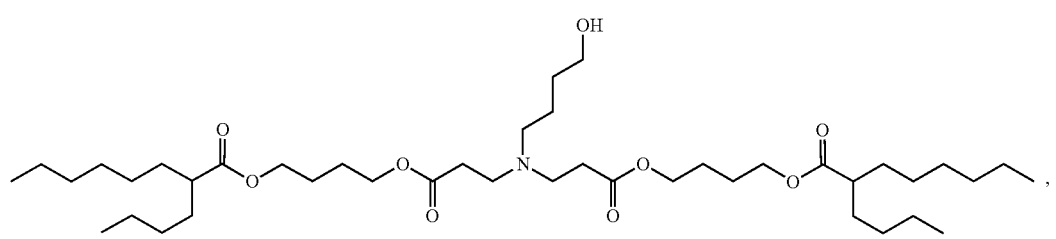
,
8
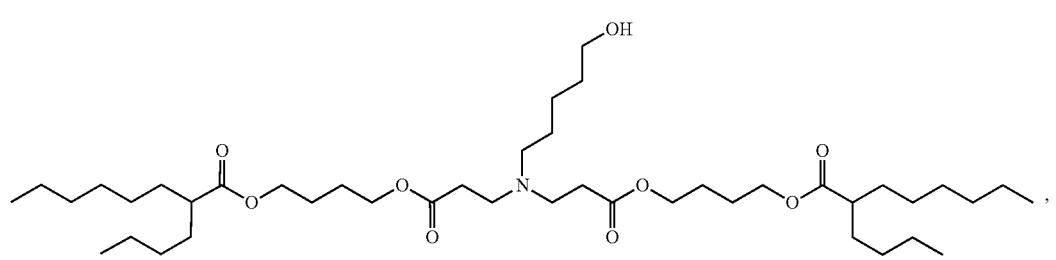
,
9
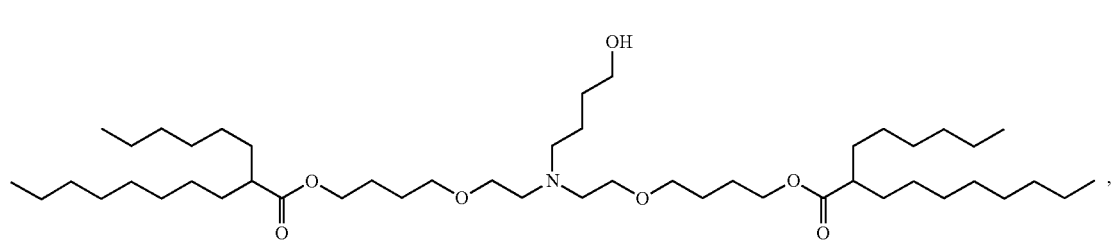
,
10
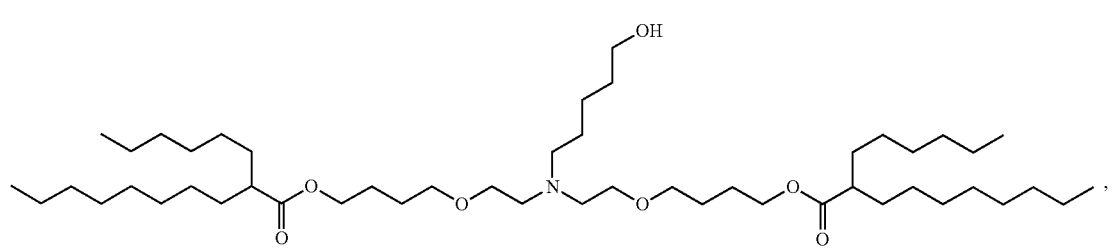
,

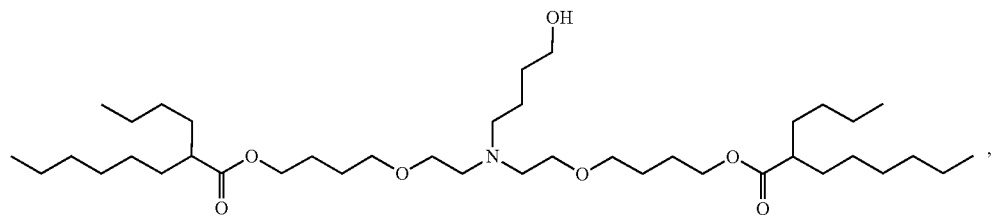
11
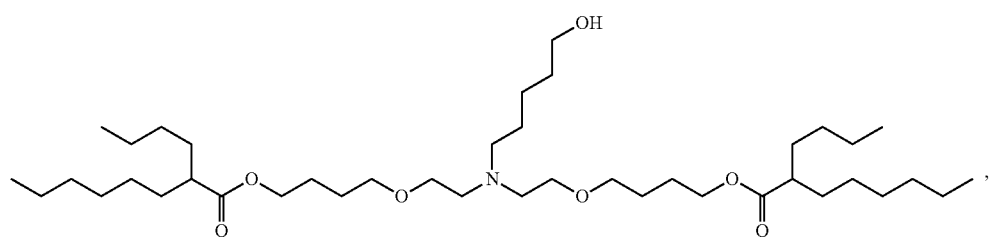
12
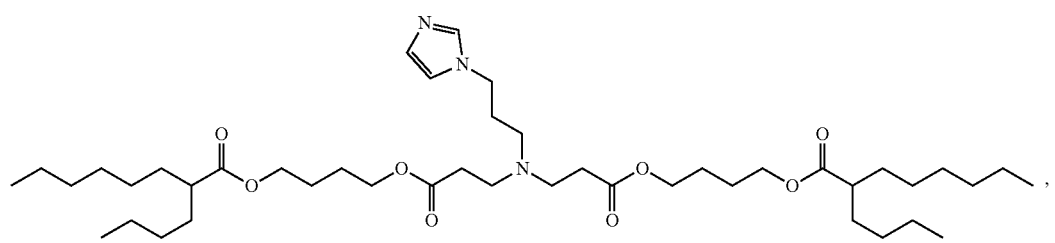
13
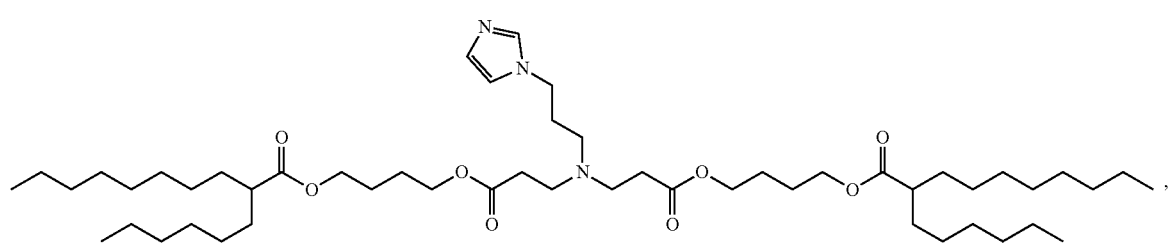
14
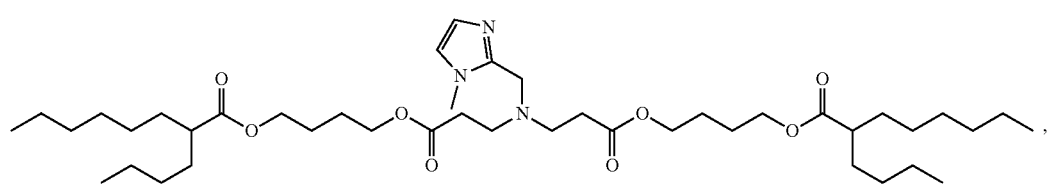
15
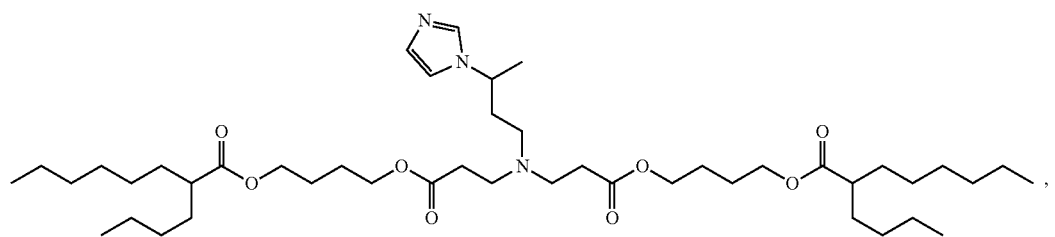
16
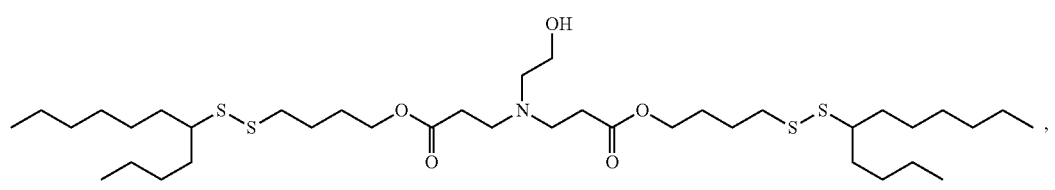
17

-continued
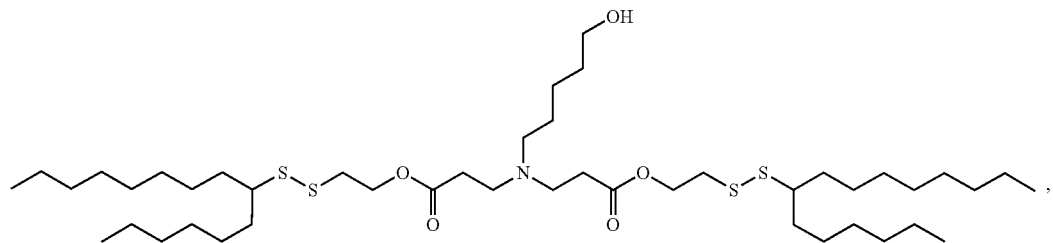
18
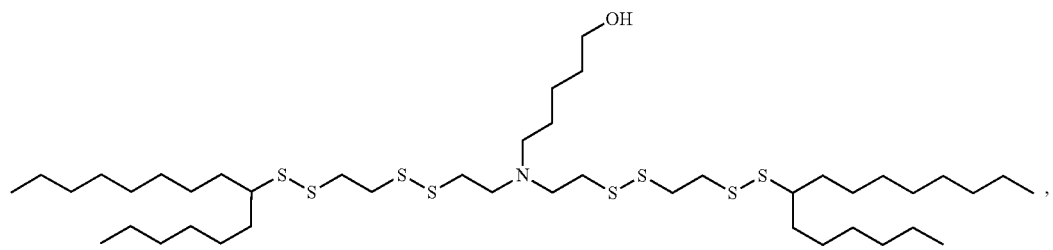
19
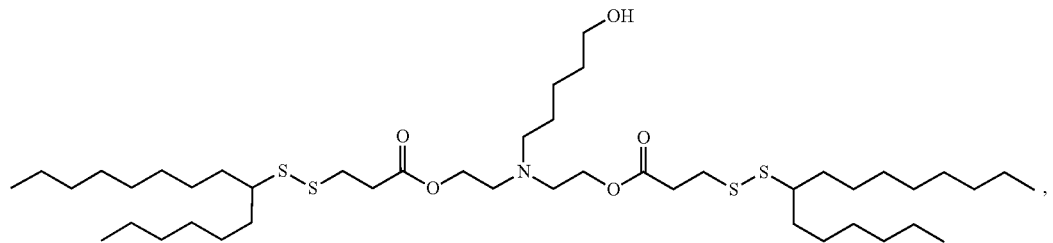
20
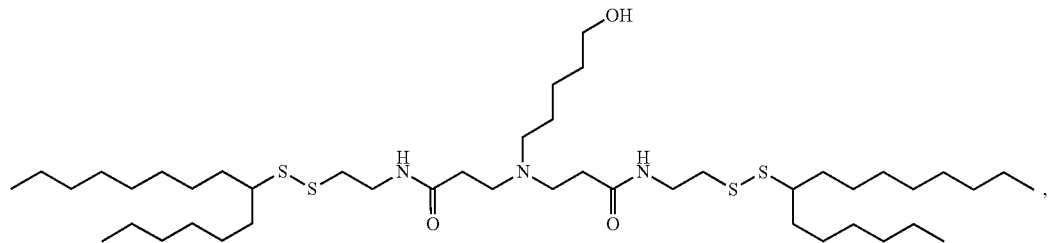
21
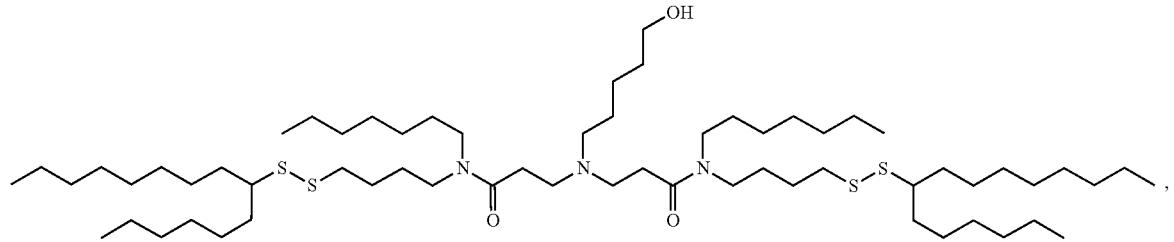
22
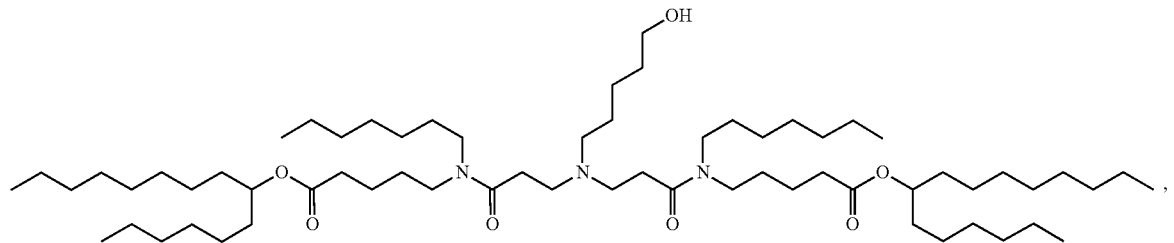
23

24
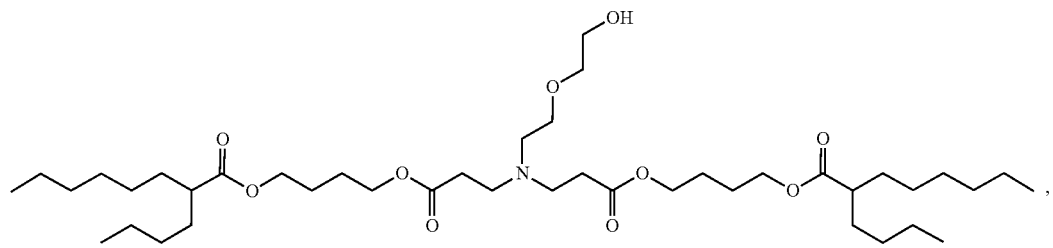
25
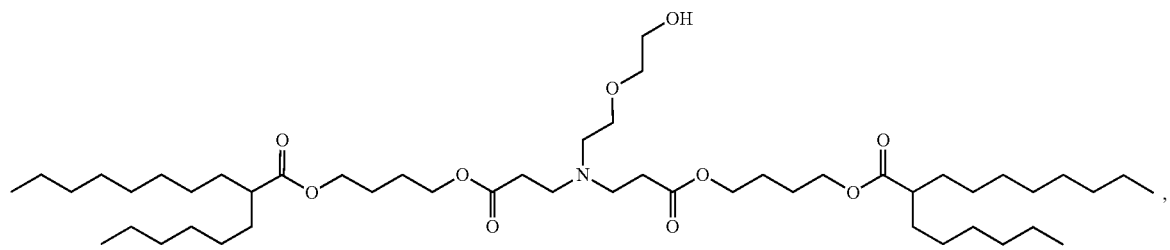
26
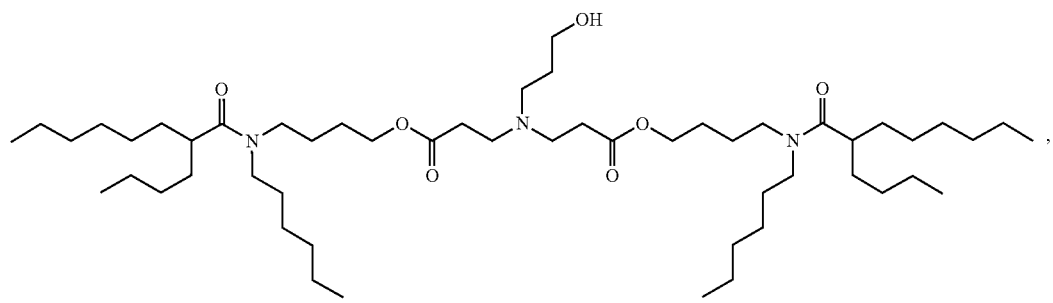
27
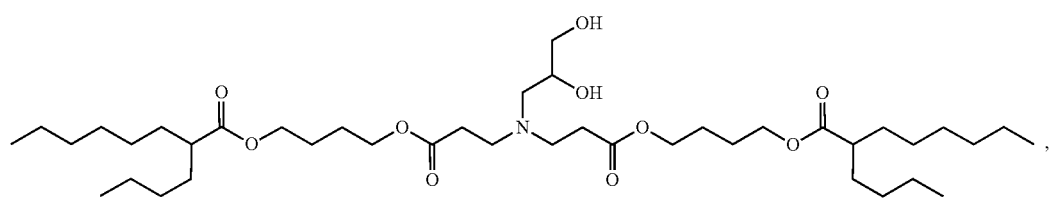
28
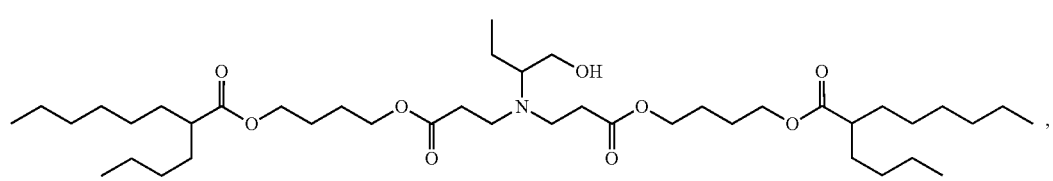
29
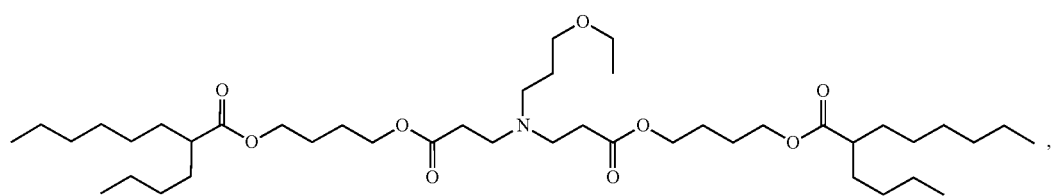
30
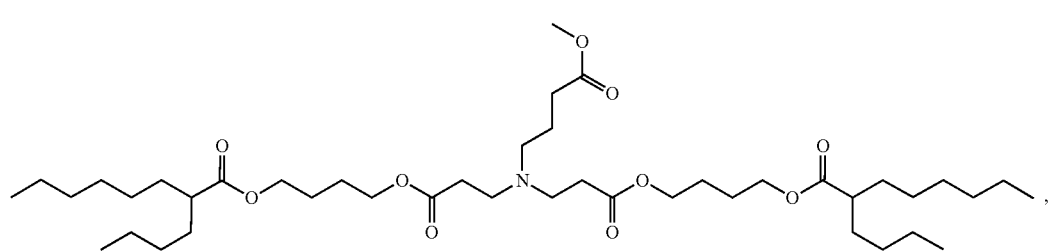

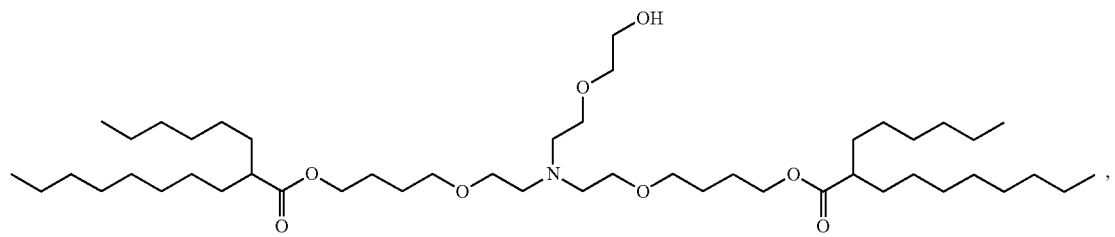
31
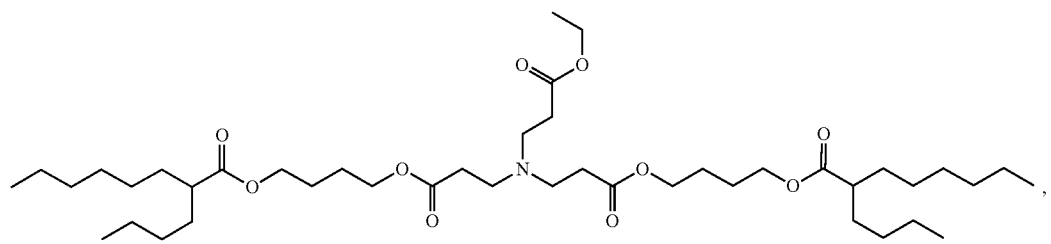
32
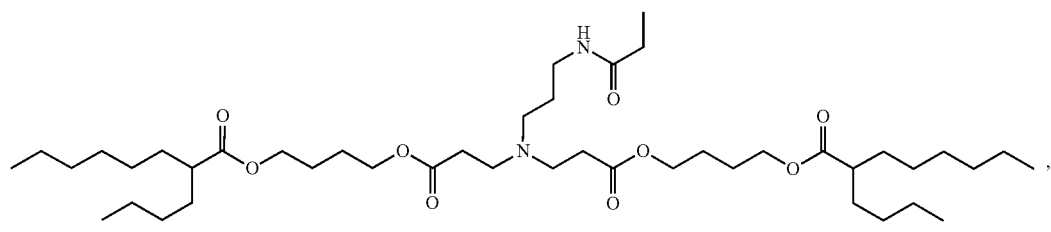
33
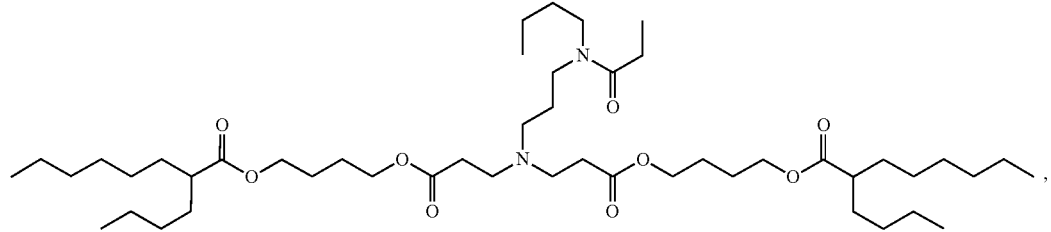
34
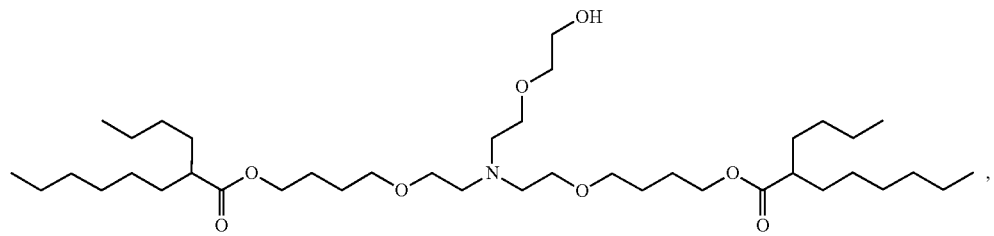
35
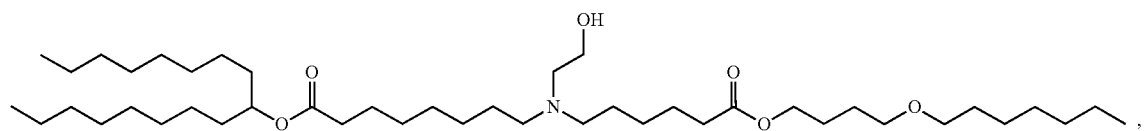
36
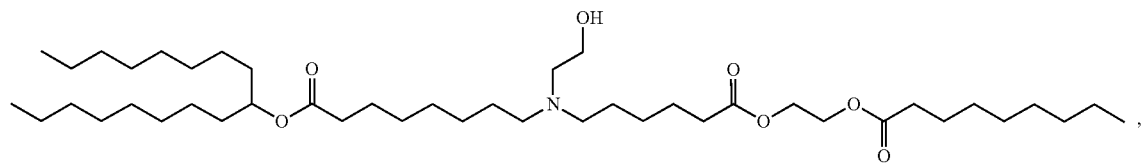
37

-continued

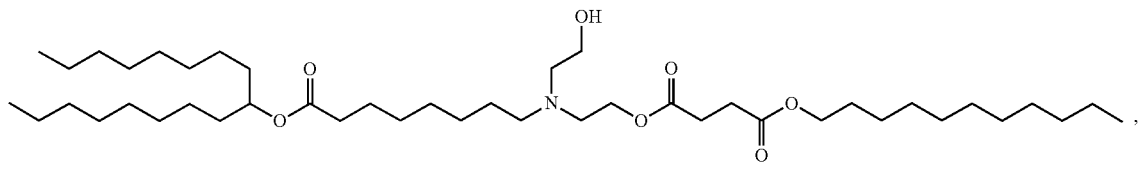

38

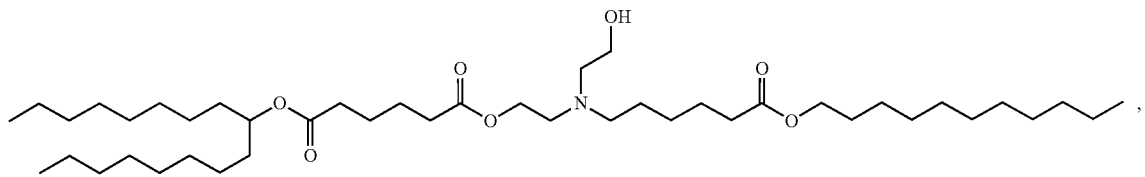

39

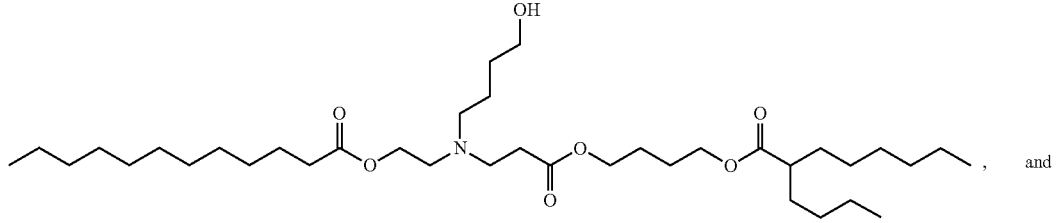

40

, and

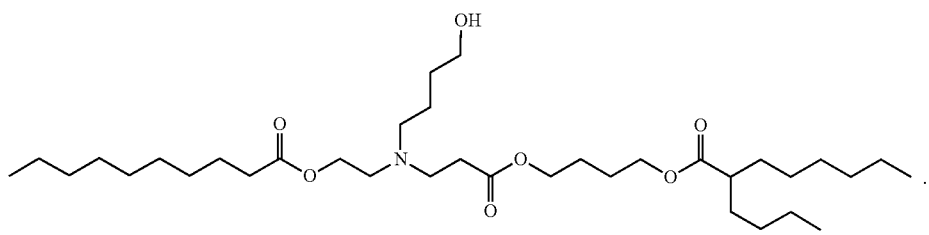

41

.

8. A lipid carrier, comprising the compound or the pharmaceutically acceptable salt, stereoisomer, or chelate thereof according to claim 1;
wherein the lipid carrier comprises a first lipid component and a second lipid component, wherein the first lipid component comprises the compound of claim 1 or the pharmaceutically acceptable salt, stereoisomer, or chelate thereof and a cationic lipid, and the second lipid component comprises one or a combination of two or more of anionic lipid, neutral lipid, sterol and amphiphilic lipid;
wherein the cationic lipid comprises one or a combination of two or more of DLinDMA, DODMA, DLin-MC2-MPZ, DLin-KC2-DMA, DOTAP, C12-200, DC-Chol and DOTMA;
the anionic lipid comprises one or a combination of two or more of phosphatidyl serine, phosphatidyl inositol, phosphatidic acid, phosphatidyl glycerol, DOPG, DOPS and dimyristoyl phosphatidylglycerol;
the neutral lipid comprises at least one of DOPE, DSPC, DPPC, DOPC, DPPG, POPC, POPE, DPPE, DMPE, DSPE and SOPE or its lipid modified by an anionic or cationic modifying group;
the amphiphilic lipid comprises one or a combination of two or more of PEG-DMG, PEG-c-DMG, PEG-C14, PEG-c-DMA, PEG-DSPE, PEG-PE, PEG-modified ceramide, PEG-modified dialkylamine, PEG-modified diacylglycerol, Tween-20, Tween-80, PEG-DPG, PEG-s-DMG, DAA, PEG-c-DOMG and GalNAc-PEG-DSG;

wherein in the lipid carrier, a molar ratio of the first lipid component to the anionic lipid to the neutral lipid to the sterol to the amphiphilic lipid is (20-65):(0-20):(5-25):(25-55):(0.3-15); or
wherein in the first lipid component, a molar ratio of the compound or the pharmaceutically acceptable salt, stereoisomer, or chelate thereof according to claim 1 to the cationic lipid is (1-10):(0-10).

9. A nucleic acid lipid nanoparticle composition, comprising the compound or the pharmaceutically acceptable salt, stereoisomer, or chelate thereof according to claim 1, and a nucleic acid drug;
wherein the nucleic acid drug comprises one or a combination of two or more of DNA, siRNA, mRNA, dsRNA, antisense nucleic acid, microRNA, antisense microRNA, antagomir, a microRNA inhibitor, a microRNA activator and immunostimulatory nucleic acid; or
wherein a mass ratio of the nucleic acid drug to the compound or the pharmaceutically acceptable salt, stereoisomer, or chelate thereof according to claim 1 is 1:(3-40).

10. A nucleic acid lipid nanoparticle composition, comprising the lipid carrier according to claim 8, and a nucleic acid drug;
wherein the nucleic acid drug comprises one or a combination of two or more of DNA, siRNA, mRNA, dsRNA, antisense nucleic acid, microRNA, antisense microRNA, antagomir, a microRNA inhibitor, a microRNA activator and immunostimulatory nucleic acid; or wherein a mass ratio of the nucleic acid drug to the lipid carrier according to claim 8 is 1:(3-40).

11. A pharmaceutical preparation, comprising the compound or the pharmaceutically acceptable salt, stereoisomer, or chelate thereof according to claim 1, as well as a pharmaceutically acceptable excipient, carrier and diluent agent;
   wherein the pharmaceutical preparation has a particle size of 30-500 nm; or
   wherein the entrapment efficiency of the nucleic acid drug in said pharmaceutical preparation is greater than 50%.

12. A pharmaceutical preparation, comprising the lipid carrier according to claim 8, as well as a pharmaceutically acceptable excipient, carrier and diluent agent;
   wherein the pharmaceutical preparation has a particle size of 30-500 nm; or
   wherein the entrapment efficiency of the nucleic acid drug in said pharmaceutical preparation is greater than 50%.

13. A pharmaceutical preparation, comprising the nucleic acid lipid nanoparticle composition according to claim 9, as well as a pharmaceutically acceptable excipient, carrier and diluent agent;
   wherein the pharmaceutical preparation has a particle size of 30-500 nm; or
   wherein the entrapment efficiency of the nucleic acid drug in said pharmaceutical preparation is greater than 50%.

14. A lipid carrier, comprising the compound or the pharmaceutically acceptable salt, stereoisomer or chelate thereof according to claim 7;
   wherein the lipid carrier comprises a first lipid component and a second lipid component, wherein the first lipid component comprises the compound or the pharmaceutically acceptable salt, stereoisomer, or chelate thereof according to claim 9 and cationic lipid, and the second lipid component comprises one or a combination of two or more of anionic lipid, neutral lipid, sterol and amphiphilic lipid;
   wherein the cationic lipid comprises one or a combination of two or more of DLinDMA, DODMA, DLin-MC2-MPZ, DLin-KC2-DMA, DOTAP, C12-200, DC-Chol and DOTMA;
   the anionic lipid comprises one or a combination of two or more of phosphatidyl serine, phosphatidyl inositol, phosphatidic acid, phosphatidyl glycerol, DOPG, DOPS and dimyristoyl phosphatidylglycerol;
   the neutral lipid comprises at least one of DOPE, DSPC, DPPC, DOPC, DPPG, POPC, POPE, DPPE, DMPE, DSPE and SOPE or its lipid modified by an anionic or cationic modifying group;
   the amphiphilic lipid comprises one or a combination of two or more of PEG-DMG, PEG-c-DMG, PEG-C14, PEG-c-DMA, PEG-DSPE, PEG-PE, PEG-modified ceramide, PEG-modified dialkylamine, PEG-modified diacylglycerol, Tween-20, Tween-80, PEG-DPG, PEG-s-DMG, DAA, PEG-c-DOMG and GalNAc-PEG-DSG;
   wherein in the lipid carrier, a molar ratio of the first lipid compound to the anionic lipid to the neutral lipid to the sterol to the amphiphilic lipid is (20-65):(0-20):(5-25):(25-55):(0.3-15); or
   wherein in the first lipid component, a molar ratio of the compound or the pharmaceutically acceptable salt, stereoisomer, or chelate thereof according to claim 9 to the cationic lipid is (1-10):(0-10).

15. A nucleic acid lipid nanoparticle composition, comprising the compound or the pharmaceutically acceptable salt, stereoisomer, or chelate thereof according to claim 7, and a nucleic acid drug;
   wherein the nucleic acid drug comprises one or a combination of two or more of DNA, siRNA, mRNA, dsRNA, antisense nucleic acid, microRNA, antisense microRNA, antagomir, a microRNA inhibitor, a microRNA activator and immunostimulatory nucleic acid; or
   wherein a mass ratio of the nucleic acid drug to the compound or the pharmaceutically acceptable salt, stereoisomer, or chelate thereof according to claim 9 is 1:(3-40).

16. A nucleic acid lipid nanoparticle composition, comprising the lipid carrier according to claim 14, and a nucleic acid drug;
   wherein the nucleic acid drug comprises one or a combination of two or more of DNA, siRNA, mRNA, dsRNA, antisense nucleic acid, microRNA, antisense microRNA, antagomir, a microRNA inhibitor, a microRNA activator and immunostimulatory nucleic acid; or
   wherein a mass ratio of the nucleic acid drug to the lipid carrier according to claim 14 is 1:(3-40).

17. A pharmaceutical preparation, comprising the compound or the pharmaceutically acceptable salt, stereoisomer, or chelate thereof according to claim 7, as well as a pharmaceutically acceptable excipient, carrier and diluent agent;
   wherein the pharmaceutical preparation has a particle size of 30-500 nm; or
   wherein the entrapment efficiency of the nucleic acid drug in said pharmaceutical preparation is greater than 50%.

18. A pharmaceutical preparation, comprising the nucleic acid lipid nanoparticle composition according to claim 15, as well as a pharmaceutically acceptable excipient, carrier and diluent agent;
   wherein the pharmaceutical preparation has a particle size of 30-500 nm; or
   wherein the entrapment efficiency of the nucleic acid drug in said pharmaceutical preparation is greater than 50%.

* * * * *